United States Patent
Sumi

(10) Patent No.: US 10,683,477 B2
(45) Date of Patent: Jun. 16, 2020

(54) SPHEROID-PRODUCING DEVICE, METHOD FOR RECOVERING SPHEROIDS, AND METHOD FOR PRODUCING SPHEROIDS

(71) Applicant: Corning Incorporated, Corning, NY (US)

(72) Inventor: Shoichiro Sumi, Kyoto (JP)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 15/121,322

(22) PCT Filed: Feb. 25, 2015

(86) PCT No.: PCT/JP2015/000950
§ 371 (c)(1),
(2) Date: Aug. 24, 2016

(87) PCT Pub. No.: WO2015/129263
PCT Pub. Date: Sep. 3, 2015

(65) Prior Publication Data
US 2017/0015966 A1     Jan. 19, 2017

(30) Foreign Application Priority Data
Feb. 25, 2014   (JP) ................. 2014-034577

(51) Int. Cl.
C12M 3/00          (2006.01)
C12M 1/00          (2006.01)
(Continued)

(52) U.S. Cl.
CPC ............ *C12M 25/01* (2013.01); *C12M 47/02* (2013.01); *C12N 5/00* (2013.01); *C12N 5/0062* (2013.01); *C12N 2511/00* (2013.01)

(58) Field of Classification Search
CPC ...... C12M 23/20; C12M 25/06; C12M 21/08; C12M 23/04
See application file for complete search history.

(56) References Cited

U.S. PATENT DOCUMENTS 6,027,695 A * 2/2000 Oldenburg ............ B01L 3/5085
                                                       422/504
8,575,312 B2   11/2013 Behrens et al.
(Continued)

FOREIGN PATENT DOCUMENTS

CN    102257123 A    11/2011
JP    2012-502636 A   2/2012
(Continued)

OTHER PUBLICATIONS

Tung, Y-C. et al. 2011. High-throughput 3D spheroid culture and drug testing using a 384 hanging drop array. Analyst 136: 473-478. specif. pp. 473, 474.*
(Continued)

*Primary Examiner* — Nathan A Bowers
(74) *Attorney, Agent, or Firm* — Annie J. Kock; Elias Charles Sayre

(57) ABSTRACT

The present invention provides a device for producing a large number of uniform spheroids by an easy method. The spheroid-producing device (1) at least includes a first surface (11), a second surface (12), and a plurality of wall surfaces (13). The second surface (12) faces the first surface (11). The respective wall surfaces (13) constitute a plurality of holes penetrating through the first surface and the second surface. In addition, an equivalent diameter of inscribed circles of openings in the first surface (11) is greater than an equivalent diameter of inscribed circles of openings in the second surface (12).

19 Claims, 27 Drawing Sheets

(51) Int. Cl.
  *B01L 3/00* (2006.01)
  *C12M 1/12* (2006.01)
  *C12N 5/00* (2006.01)

(56) References Cited

U.S. PATENT DOCUMENTS

| | | | |
|---|---|---|---|
| 2006/0281172 A1* | 12/2006 | Kuwabara | C12M 23/10 435/305.2 |
| 2010/0297767 A1 | 11/2010 | Hattori et al. | |
| 2011/0306122 A1* | 12/2011 | Moritz | B01L 3/5085 435/325 |
| 2013/0040855 A1* | 2/2013 | Takayama | B01L 3/50853 506/10 |
| 2013/0203159 A1 | 8/2013 | Itoh et al. | |

FOREIGN PATENT DOCUMENTS

| | | |
|---|---|---|
| JP | 5074382 B2 | 11/2012 |
| JP | 2013-517809 A | 5/2013 |
| KR | 10-2007-0075006 A | 7/2007 |
| KR | 10-0785049 B1 | 12/2007 |
| KR | 10-2013-0033938 A1 | 4/2013 |
| WO | WO 2007/114351 A1 | 10/2007 |
| WO | WO 2010/031194 A1 | 3/2010 |
| WO | WO 2013/047974 A1 | 4/2013 |
| WO | WO 2014/165273 A1 | 10/2014 |

OTHER PUBLICATIONS

96 Well Microplates—Corning Inc. http://csmedia2.corning.com/lifesciences/media/eguipment_compatibility/MD_Microplate_Dimension_Sheets_96_Well.pdf (Year: 2016).*

384 Well Microplates—Corning Inc. http://csmedia2.corning.com/lifesciences/media/eguipment_compatibility/MD_Microplate_Dimension_Sheets_384_Well.pdf (Year: 2016).*

1536 Well Microplates—Corning Inc. https://www.corning.com/catalog/cls/documents/drawings/MD_Microplate_Dimension_Sheets_ 1536_Well.pdf (Year: 2016).*

Combined Office Action and Search Report dated May 18, 2017 in Chinese Patent Application No. 201580010448.4 (with Partial English translation and English translation of categories of cited documents).

International Search Report dated Jun. 2, 2015, in PCT/JP2015/000950 filed Feb. 25, 2015.

K. M. Yamada et al., "Modeling Tissue Morphogenesis and Cancer in 3D", Cell 130, (Aug. 24, 2007), pp. 601-610.

E. Eschbach et al., Microstructured Scaffolds for Liver Tissue Cultures of High Cell Density: Morphological and Biochemical Characterization of Tissue Aggregates, Journal of Cellular Biochemistry, vol. 95, (2005), pp. 243-255.

C. L. Bauwens et al., "Control of Human Embryonic Stem Cell Colony and Aggregate Size Heterogeneity Influences Differentiation Trajectories", Stem Cells, vol. 26, (2008), pp. 2300-2310.

S. Rungarunlert et al., "Embryoid body formation from embryonic and induced pluripotent stem cells: Benefits of bioreactors", World Journal of Stem Cells, vol. 1(1), (Dec. 2009), pp. 11-21.

S.R. Horman, et al., "3D High-Content Analysis of Spheroids New Methodology Shown to Improve Screening", Genetic Engineering & Biotechnology News, Tutorials, vol. 33, No. 16, (Sep. 15, 2013), 3 pages.

S. Sumi et al., "New Culturing Equipment for Effectively Generating High-quality Cell Aggregation—Development of Entire Surface Multi-hole Type Culturing Surface", Multi-Hole Type Culturing Surface, vol. 14, Suppl. 0-52-2, (Feb. 1, 2015), with English Translation, 5 pages.

Extended Search Report dated Oct. 12, 2017 in European Patent Application No. 15755340.5.

Written Opinion dated Oct. 24, 2017 in Singaporean Patent Application No. 11201606992P.

Machine Translation of JP2016505070 Office Action dated May 13, 2019, Japan Patent Office, 2 Pgs.

\* cited by examiner

Fig. 23
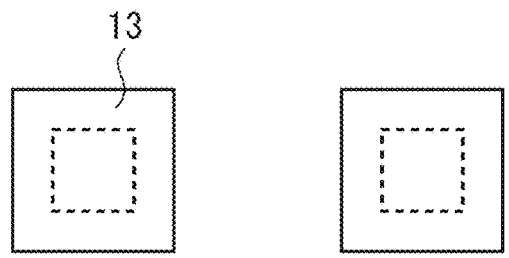
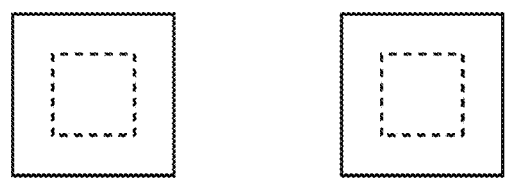
Fig. 24
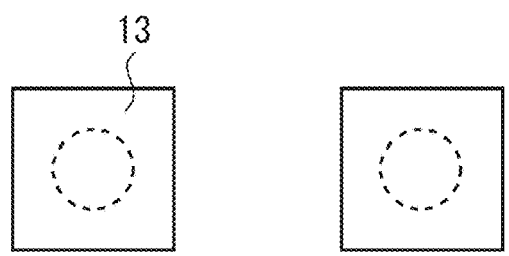
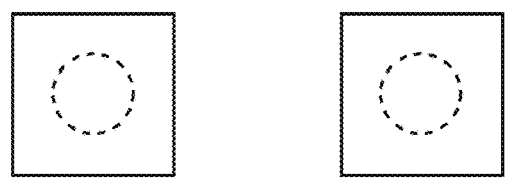

Fig. 25
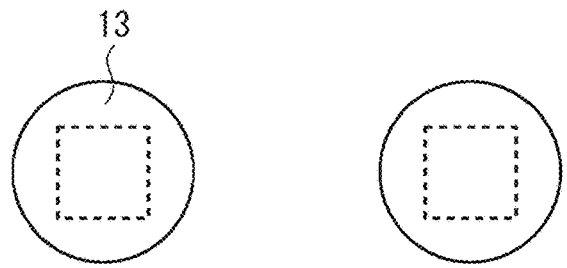
Fig. 26
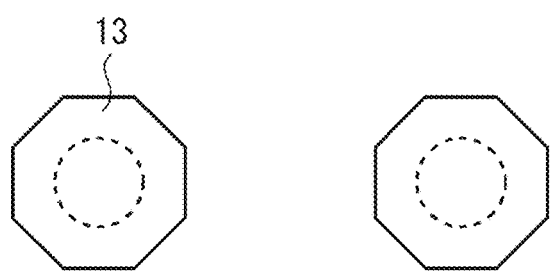
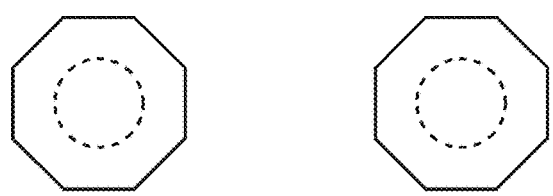

×7.5

×75

×10

SPHEROID-PRODUCING DEVICE, METHOD FOR RECOVERING SPHEROIDS, AND METHOD FOR PRODUCING SPHEROIDS

TECHNICAL FIELD

The present invention relates to a device suitable for culturing spheroids with a uniform size in large numbers and in high density and a method using the device.

BACKGROUND ART

Non patent literature 1 indicates that the three-dimensional culture method is available for reproducing the functions of living tissues more accurately than the two-dimensional culture method. Non patent literature 1 also indicates that the three-dimensional culture method is one of methods useful for efficiently differentiating pluripotent stem cells and iPS cells. Attempts are being made to rebuild and complement lost functions by returning three-dimensionally cultured artificial tissues into a body using such a technique. Moreover, other attempts are being made to apply such a technique to regenerative medicine for assistance of damaged tissue repair. Further attempts are being made to use such a technique for testing toxicity of pharmaceutical agents. In particular, large-scale production of cell aggregates that are uniform in size and shape is required for regenerative medicine and its research. In addition, a method with higher convenience and lower cost than existing methods will become necessary.

[Significance of Producing Uniform Sized and Shaped Cell Aggregates]

In the case of liver cells, there is a problem that in vivo functions cannot be reproduced in vitro. One example of this problem is that the drug metabolism function inherent in liver cells is deteriorated when the liver cells are two-dimensionally cultured. One of means for addressing this problem is a method for forming cell aggregates as disclosed in Non-patent literature 2. Non patent literature 2 indicates that the function of the cell aggregates produced by this method is dramatically improved from those of the two-dimensionally cultured cells.

When embryonic stem cells or induced pluripotent stem cells are differentiated into target cells in vitro, cell aggregates called embryoid bodies is formed, followed by the initiation of the program of development and differentiation, to thereby differentiate embryonic stem cells OF induced pluripotent stem cells into target cells. Non patent literature 3 reports that size of cell aggregates influence the directions of differentiation.

[Regarding Technique for Producing a Large Number of Uniform Size and Shape Cell Aggregates]

Non patent literature 4 discloses a culture method called the hanging drop method in which culture is performed in droplets. Non patent literature 4 further discloses a U or V bottomed low adherence plate. Non patent literature 4 also discloses a large-scale culture method using bioreactors. The hanging drop method, U bottomed plate and the like are suitable for producing cell aggregates that are uniform in size and shape. On the other hand, the hanging drop method, U bottomed plate and the like are not suitable for large-scale culture because they allow only one cell aggregate to be produced in one well. Although the hanging drop method is widely applied to research, it is not suitable for large-scale culture for producing more than several hundred or several thousand order of cell aggregates at a time.

Non patent literature 4 discloses a method using a low adherence container. Non patent literature 4 also discloses a development of a method using roller bottle. Further disclosed is a development of a method for immobilizing cells in a gel or beads so as to carry out suspension culture. Although these methods enable several thousand cell aggregates to be produced with a high density, there is a problem that the produced cell aggregates are heterogeneous. Roller bottles in low rotation that are capable of large-scale production of comparatively homogeneous cell aggregates are being developed. However, these methods require a large-scale apparatus accompanied with complicated operation. Further, even though the rotation speed of roller bottles or the like is controlled precisely, any adjacent cells and cell aggregates may be irregularly associated with each other to form another cell aggregates in a solution. It is thus difficult to produce uniform size cell aggregates.

For example, patent literature 1 discloses an example of a method for producing a group of cell aggregates in a large number and with convenience. In this group, morphological features such as size and shape of the cell aggregates and properties outside cells are homogeneous. In the method disclosed in patent literature 1, a culture solution containing cells is poured into a hollow part of a structural member, wherein at least one lower end of the hollow part is opened. At this time, a portion of the culture solution is made to project downward from the open end. In this method, the cells are cultured in the projecting portion of the culture solution. This method has a problem for pouring the culture solution into the hollow part when an upper end of the hollow part is closed. Another problem of this method is that a process for forming the projecting portion of the culture solution is complicated. Moreover, a problem in this process is that it is necessary to accurately adjust an amount of pouring. Although the pouring (suction) of the culture solution can be efficiently carried out when both ends of the hollow part are open, there is another problem in this method. The problem is that the upper end needs to be closed or a mechanism for maintaining a suction pressure needs to be further included in order to maintain a state of the culture solution that has been poured into. New limitations are imposed on this manner since an amount of the culture solution that can be involved in metabolism of the cells is regulated by a volume of the hollow part. One of the new limitations is that a cell concentration and a culture period are limited by the metabolic activity of a cell for use. The available size of cell aggregates and types of cells are also limited by this new limitation. Patent Literature 2 discloses a suspension plate that allows easier pouring of a culture solution than that in the technique disclosed in Patent literature 1. Patent literature 2 discloses a structure in which a culture solution is communicated from a first surface with a second surface. However, with the manner disclosed in patent literature 2, the number of pouring operations is increased in proportion to the number of cell aggregates to be created. Accordingly, the problem of complicated operations still remains.

CITATION LIST

Patent Literature

Patent Literature 1: Japanese Patent No. 5074382
Patent Literature 2: International Patent Publication No. WO 2010/031194

Non Patent Literature

Non Patent Literature 1: Kenneth M. Yamada, et al. "Modeling Tissue Morphogenesis and Cancer in 3D", Cell 130, Sep. 24, 2007, pp. 601-610 Non Patent Literature 2: Erik Eschbach et al., "Microstructured Scaffolds for Liver Tissue Cultures of High Cell Density: Morphological and Biochemical Characterization of Tissue Aggregates", Journal of Cellular Biochemistry 95, 2005, pp. 243-255

Non Patent Literature 3: C L Bauwens, et al. "Control of Human Embryonic Stem Cell Colony and Aggregate Size Heterogeneity influences Differentiation Trajectories", Stem Cells 26, 2008, pp. 2300-2310

Non Patent Literature 4: Sasitorn Rungarunlert, et al. "Embryoid body formation from embryonic and induced pluripotent stem cells: Benefits of bioreactors", World Journal of Stem Cells 1(1), Dec. 31, 2009, pp. 11-21

SUMMARY OF INVENTION

Technical Problem

As described above, the conventional culture method using the container for the hanging drop method and the culture method using the rotary bottles have advantage and drawback. It has thus been difficult to produce a large number of cell aggregates that are uniform in shape and size. Large-scale production, which is several hundred or thousand order, of such cell aggregates has been particularly difficult.

The present invention has been made in light of the above problems.

Solution to Problem

The present inventors have investigated a physical phenomenon occurring between a device for culturing cells and a culture medium. As a result of the investigation, the present inventors have achieved a device for producing spheroids with a convenient method.

In an exemplary aspect of the present invention, a spheroid-producing device includes at least a first surface, a second surface, and a plurality of wall surfaces. The second surface is a back side surface of the first surface. The respective wall surfaces constitute a plurality of holes penetrating through the first surface and the second surface. In addition, an equivalent diameter of inscribed circles of openings in the first surface is greater than an equivalent diameter of inscribed circles of openings in the second surface. According to the above exemplary aspect, it is possible to provide a device suitable for easily producing a large number of spheroids. This device enables a culture medium to be poured from the first surface that is disposed on an upper side and produced spheroids to be recovered from the second surface that is disposed on a lower side. This facilitates seeding process of cells and culturing process of the cells. It is thus possible to reduce times required for these processes. Additionally, there are following advantages in forming holes in the spheroid-producing device in which the diameter of the holes is increased from the second surface toward the first surface. Firstly, a culture solution can be easily infiltrated into the device from the first surfaces toward the second surface. Secondly, as the density of the settled cells will become greater near the second surface, spheroids formation can be promoted. In addition to the above advantages, it will become easy to manufacture the device itself.

In another exemplary aspect of the spheroid-producing device, an equivalent diameter of inscribed circles of openings formed by the holes is preferably greater than a length of an equivalent diameter of inscribed circles of openings in the second surface. The equivalent diameter of the inscribed circles of the openings in the second surface is preferably within a range of 200 micrometers to 1 cm. At least portions of the respective wall surfaces preferably include inclinations with an angle greater than one degree and smaller than 90 degrees with respect to the second surface. When a hydrophobic material is used, it is preferable to determine an equivalent radius of the circumscribed circles (a length half of the equivalent diameter) of the openings in the second surface in consideration of a contact angle between the material of the device and the culture medium. When a hydrophilic material is used, it is preferable to determine an equivalent radius of the inscribed circles of the openings in the second surface in consideration of the contact angle between the material of the device and the culture medium.

In another exemplary aspect of a method for recovering spheroids that are produced by using the above mentioned spheroid-producing device, the method includes bringing the second surface of the spheroid-producing device into contact with a solution selected from water, a culture medium, and a buffer solution in order to recover spheroids. Alternatively, the method includes applying a pressure on the first surface of the spheroid-producing device in order for spheroids to be retrieved through the openings in the second surface. According to either of the recovery methods, it is possible to easily recover spheroids without damaging the spheroids.

In still another exemplary aspect of a method for producing spheroids using the above-mentioned spheroid-producing device, the method includes pouring a culture medium containing cells in the respective holes from the first surface, forming droplets in the respective holes, and culturing the cells in the droplets in order to produce spheroids. It is preferable to use the above-mentioned recovery methods in order to recover the spheroids produced by this method.

Advantageous Effects of Invention

The exemplary aspect of the present invention is a spheroid-producing device, a method for recovering spheroids, and a method for producing spheroids that are suitable for large-scale production of uniform spheroids by an easy technique. The exemplary aspect of the present invention can provide an easy method suitable for producing a large number of uniform spheroids.

BRIEF DESCRIPTION OF DRAWINGS

FIG. 23 is a drawing showing an example of a shape of openings in the spheroid-producing device;

FIG. 24 is a drawing showing another example of the shape of the openings in the spheroid-producing device;

FIG. 25 is a drawing showing another example of the shape of the openings in the spheroid-producing device;

FIG. 26 is a drawing showing another example of the shape of the openings in the spheroid-producing device;

DESCRIPTION OF EMBODIMENTS

Figure 1:
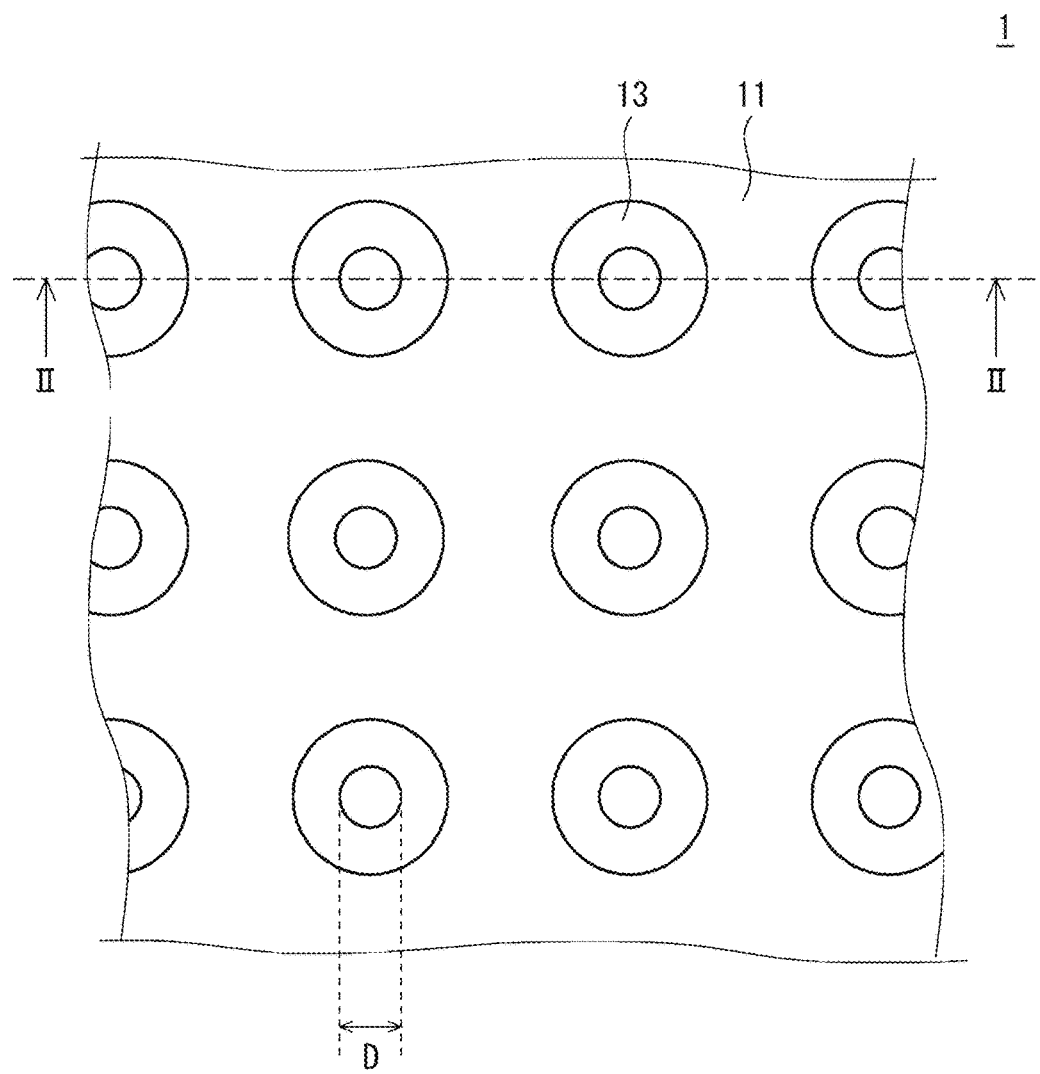
FIG. 1 is a drawing showing an example of a spheroid-producing device according to an exemplary embodiment.

Hereinafter, exemplary embodiment will be described with reference to the drawings. To clarify the description, some parts thereof and some of the drawings have been omitted or simplified as appropriate. Note that in the drawings, elements having the same configuration or function and corresponding parts are denoted by the same reference signs, and repeated descriptions will be omitted.

First Exemplary Embodiment

Figure 2:
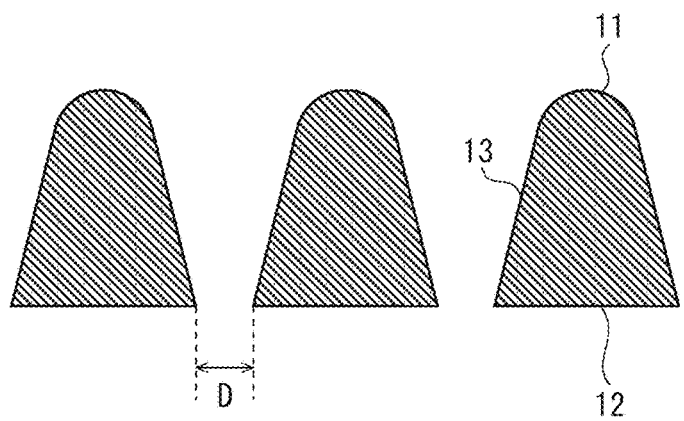
FIG. 2 is a cross-sectional diagram taken along the line 11-II of the spheroid-producing device shown in FIG. 1.

FIG. 1 is an example of a spheroid-producing device according to an exemplary embodiment. FIG. 2 is a cross-sectional diagram taken along the line of the spheroid-producing device shown in FIG. 1. A spheroid-producing device 1 is a device for producing spheroids by culturing cells in a culture medium shaped in a droplet form and then aggregating cells in order to obtain the spheroids. A spheroid is a large number of aggregated cells in three dimensions.

The spheroid-producing device 1 includes at least a first surface 11, a second surface 12, and wall surfaces 13. FIG. 1 is a drawing showing the spheroid-producing device 1 when it is viewed from a side of the first surface 11.

The first surface 11 is an upper surface of the spheroid-producing device 1 and is a surface that is on an upper side when a culture medium and the like are poured in order to culture cells.

The second surface 12 is a surface that faces the first surface 11. The second surface 12 forms a bottom (a bottom surface) of the spheroid-producing device 1 and is a back side surface of the upper surface (the first surface 11).

The wall surfaces 13 form holes (through holes) penetrating through the first surface 11 and the second surface 12. Further, the wall surfaces 13 serve to form openings in the first surface 11 and the second surface 12 and to allow the first surface 11 to communicate with the second surface 12.

In addition, in the spheroid-producing device 1, the holes formed by the wall surfaces 13 are designed in such a way that openings thereof formed closer to the second surface 12 will become smaller than the openings thereof formed closer to the first surface 11. The sizes of the openings are compared using an equivalent diameter.

The term "equivalent diameter" is used as a collective term for an equivalent diameter of an inscribed circle and an equivalent diameter of a circumscribed circle. The "equivalent diameter of the circumscribed circle" is a diameter of circles circumscribing the openings and is used as a diameter of the circumscribed circle drawn on a planar surface that is parallel to the second surface 12. For example, the diameter of the circumscribed circle drawn on a planar surface parallel to the second surface 12 is used as the equivalent diameter of the openings of the holes formed between the first surface 11 and the second surface 12. The "equivalent diameter of the inscribed circle" is a diameter of circles inscribing the openings and is used as a diameter of the inscribed circle drawn on a planar surface that is parallel to the second surface 12. For example, the diameter of the inscribed circle drawn on the planar surface parallel to the second surface 12 is used as the equivalent diameter of the openings of the holes formed between the first surface 11 and the second surface 12. A length denoted by the sign "D" in the drawings is an equivalent diameter Dout of the circumscribed circle or an equivalent diameter Din of the inscribed circle. The sign "D" does not make a clear distinction between Dout and Din.

Details of the size of the openings will be described below with reference to FIG. 3.

A configuration of the spheroid-producing device 1 will be described in more detail with reference to FIG. 3, in addition to FIGS. 1 and 2. FIG. 3 is a drawing for explaining details of the spheroid-producing device. FIG. 3 uses the cross-sectional diagram shown in FIG. 2 without the shades indicating the cross sections for easier descriptions.

The spheroid-producing device 1 is designed in consideration of at least an angle θi, the equivalent diameter Dout of the circumscribed circles of the openings in the second surface 12 or the equivalent diameter Din of the inscribed circles of the openings in the second surface 12, a material used for the device, and a culture medium 8 used for cell culture. Preferably, a thickness T and a width W may be added to the consideration.

The angle θi is an angle made by inclined surfaces of the wall surfaces 13 make with respect to the second surface 12. At least a portion of the inclined surfaces of the wall surfaces 13 may make the angle θi with respect to the second surface 12. On the other hand, the entire wall surfaces 13 that form the holes may not be inclined at the angle θi. The angle θi is preferably greater than one degree and smaller than 90 degrees and more preferably within a range of 30 to 80 degrees. This is to facilitate the culture medium 8 to be poured into the holes. Alternatively, this is for all of seeded cells to settle down to lower parts of droplets by their own weights without staying on the wall surfaces 13. It is therefore possible to efficiently culture the cells.

The thickness T is a thickness of the spheroid-producing device 1 from the first surface 11 to the second surface 12. The thickness T may be the one that can bear the weight of the culture medium 8.

The equivalent diameter Dout of the circumscribed circles of the openings in the second surface 12 is a diameter of circumscribed circles that circumscribe the openings formed in the second surface 12.

The equivalent diameter Din of the inscribed circles of the openings in the second surface 12 is a diameter of circles that inscribe the openings formed in the second surface 12. Further, an equivalent radius Rout of the circumscribed circles is a half of the lengths of the equivalent diameter Dout of the circumscribed circles. An equivalent radius Rin of the inscribed circles is a half of the lengths of the equivalent diameter Din of the inscribed circles.

In exemplary one embodiment, the equivalent diameter of the inscribed circles of the openings in the first surface 11 are designed in such a way that they will become greater than the equivalent diameter Din of the inscribed circles of the openings in the second surface 12.

In addition, the equivalent diameter Din of the inscribed circles of the openings in the second surface 12 are preferably one to ten times as great as a desired size of a spheroid (e.g., 200 μm to 1 cm). Furthermore, the greater the number of holes per unit area, the more cell aggregates can be produced in a small area. Thus, the equivalent diameter Din of the inscribed circles of the openings in the second surface 12 is more preferably one to two times as great as a desired diameter of a cell aggregate.

The width W of the upper surface is a width between the wall surface 13 that constitutes one hole and another wall surface 13 that constitutes another adjacent hole. Further, the width W of the upper surface is a width at the position where the wall surface 13 inclined at the angle θi with respect to the second surface 12 ends. In other words, the two wall surfaces 13 that constitute the adjacent holes have inclined surfaces from the second surface 12 to the first surface 11, and the width W of the upper surface can be considered as being a width at an edge that enables the inclined surfaces to have the angle θi.

Figure 3:
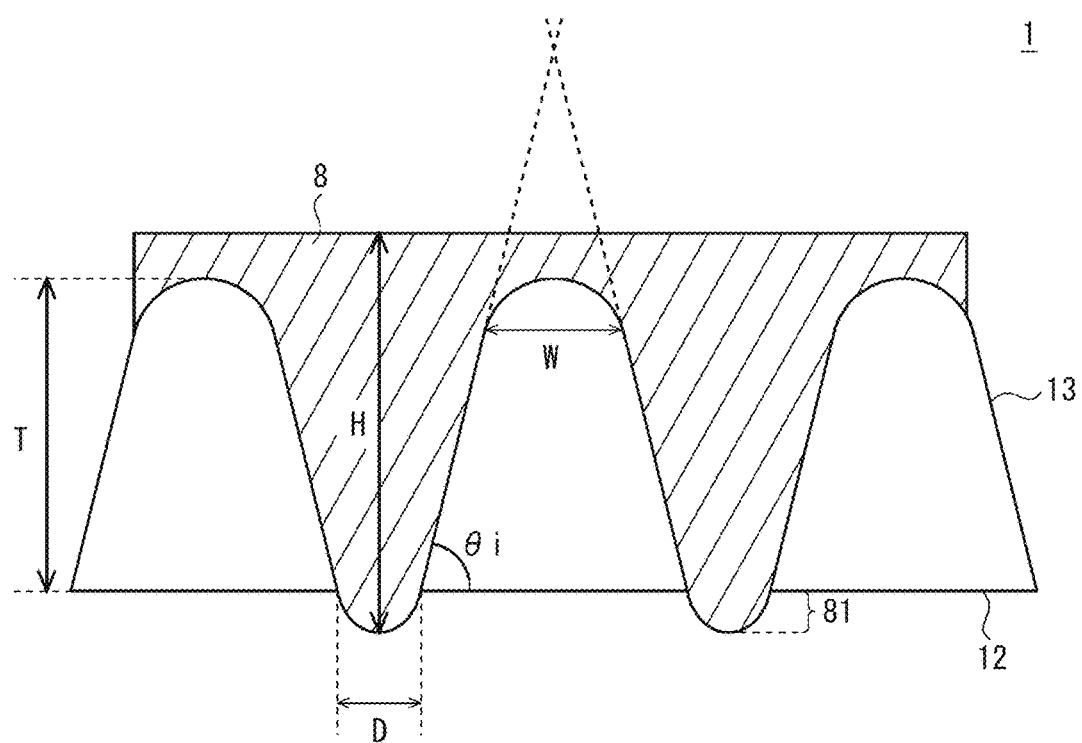
FIG. 3 is a drawing for explaining details of the spheroid-producing device.
Figure 4:
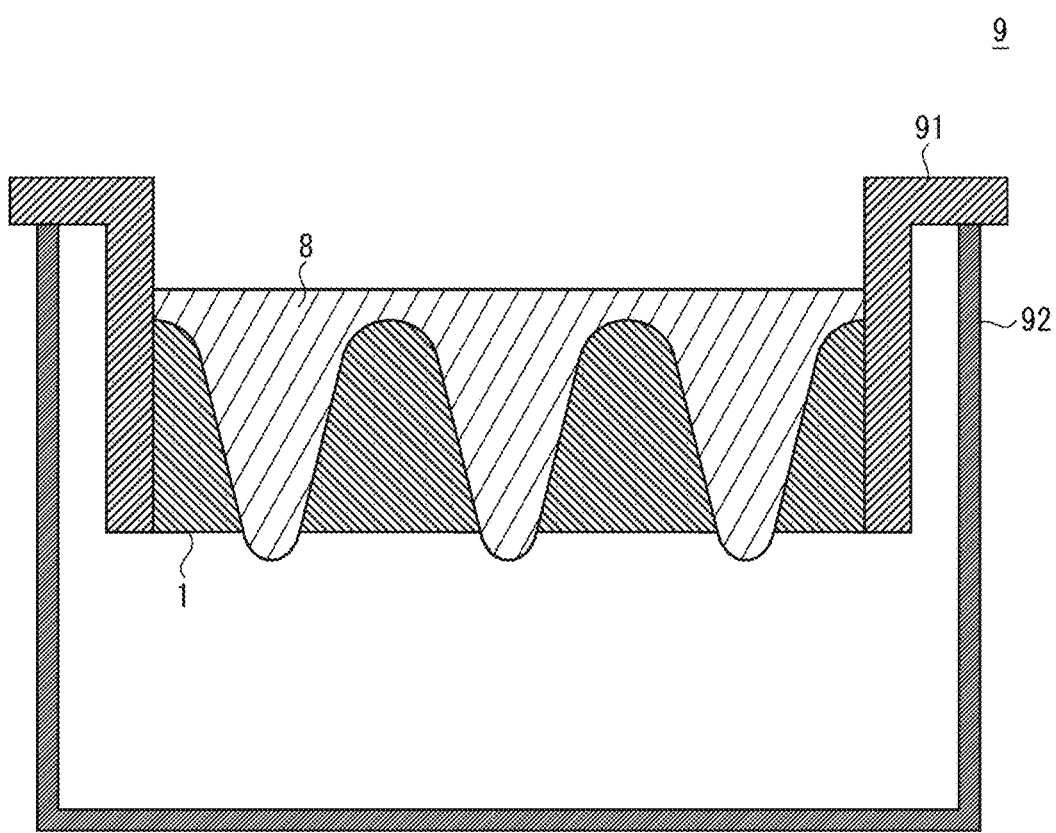
FIG. 4 is a drawing showing an example of a cell culture container that uses the spheroid-producing device according to the exemplary embodiment.

FIG. 3 schematically shows a state in which the culture medium 8 is poured into the holes and a space above the spheroid-producing device 1 from the first surface 11 (from the openings in the first surface 11) until a height (a depth) of the culture medium 8 reaches a height (a depth) H. As shown in FIG. 4, this space corresponds to a space inside a well container 91. In the configuration example of the spheroid-producing device 1 shown in FIG. 3, the culture medium 8 is poured in such a way that the culture medium 8 projects from the openings in the second surface 12. The portions projecting from the second surface 12 are droplets 81. In other words, the culture medium 8 is poured into the spheroid-producing device 1 so that the droplets 81 are formed. The droplets 81 serve as three-dimensional cell culture equipment when cells are cultured to be formed into spheroids. Downward liquid surfaces of the droplets 81 are formed as curved surfaces having a predetermined radius of curvature. A pressure difference ΔP(P-Pair) between air surrounding the droplets and liquid can be expressed by the Young-Laplace equation, namely, $\Delta P = H\rho = \gamma_L(1/r1 + 1/r2)$. In this equation, $\gamma_L$ is surface tension of the liquid [g/cm], and r1 and r2 are radii of curvature that are orthogonal to each other. If the surfaces of the droplets 81 are spherical, r1=r2 is satisfied. As these curved surfaces project downward, the droplets 81 are formed.

Figure 14:
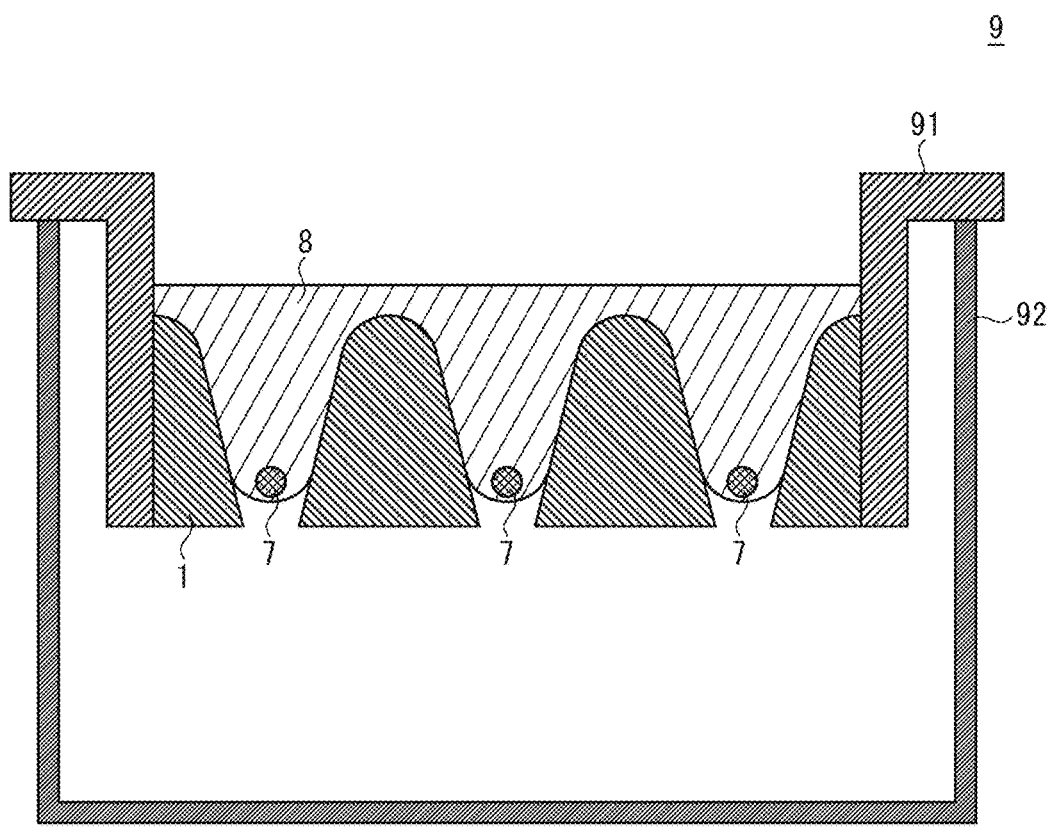
FIG. 14 is a drawing for explaining another example of the process for producing spheroids.

As a modified example of FIG. 3, when the culture medium 8 is poured from the first surface 11 (from the openings in the first surface 11), the pouring can be adjusted in such a way that the height (the depth) H of the culture medium 8 will become lower than the above height (the above depth). In such a case, in the configuration example of the spheroid-producing device 1 shown in FIG. 3, the culture medium 8 is poured in such a way that the culture medium 8 is poured halfway down the inclined surfaces (the wall surfaces 13) connecting the openings in the second surface 12 to the openings in the first surface 11. FIG. 14, which will be described later, schematically shows a state in which the culture medium 8 is poured halfway down the inclined surfaces in order to culture cells.

Details regarding the design of the spheroid-producing device such as quality of a material used for the device, properties of the culture medium used for cell culture, the equivalent diameter, and the like will be described later with reference to the drawings.

Note that in FIG. 3, to be precise, the wall surfaces 13 are surfaces that maintain the angle θi with respect to the second surface 12. Moreover, inclined surfaces between the first surface 11 and the wall surfaces 13 may be referred to as upper surfaces. Alternatively, in a broad context of the first surface 11, the first surface 11 may include a surface not parallel to the second surface 12 (an upper surface). If these terms are not concerned with an essence of the exemplary embodiment of the present invention, no clear distinctions shall be made between these terms.

FIG. 4 shows an example of a cell culture container that uses the spheroid-producing device according to the exemplary embodiment. A cell culture container 9 is an example of a basic structure of a cell culture container. In the cell culture container 9, the spheroid-producing device 1 is attached to the well container 91. A Petri-dish 92 is disposed outside the well container 91.

The spheroid-producing device 1 and the well container 91 may be made of the same material or materials different from each other. Since the well container 91 provides the space into which the culture medium 8 is poured, the well container 91 may be made of any material as long as it is not toxic to the cells. On the other hand, the Petri-dish 92 may be the one that has a shape that will not be brought into contact with the second surface 12 of the spheroid-producing device 1 and the droplets 81.

The container to which the spheroid-producing device 1 is attached is not limited to a structure shown in FIG. 4. When cells are cultured by the spheroid-producing device 1, the spheroid-producing device 1 may be attached to a multi-well plate or a Petri-dish and then used. The spheroid-producing device 1 may be used in any way as long as the second surface 12 (the bottom surface) and the droplets 81 will not be brought into contact with the multi-well plate or the Petri-dish.

Hereinafter, design of the spheroid-producing device will be described in detail. It is preferable that the following physical phenomenon is taken into consideration when the material and surfaces of the spheroid-producing device 1 and the equivalent diameter Din of the inscribed circles of the openings in the second surface 12 or the equivalent diameter Dout of the circumscribed circles of the openings in the second surface 12 are designed. In particular, the contact angle θc between the material of the wall surfaces 13 and the culture medium 8 may be preferably added to the consideration. The reason for that is the contact angle θc of the spheroid-producing device 1 is influenced by quality of the material used for the device, properties of the culture medium, and the like. In the following descriptions, firstly the design of the spheroid-producing device 1 in consideration of the physical phenomenon related to the contact angle θc will be investigated. After that, other elements will be described.

Figure 6:
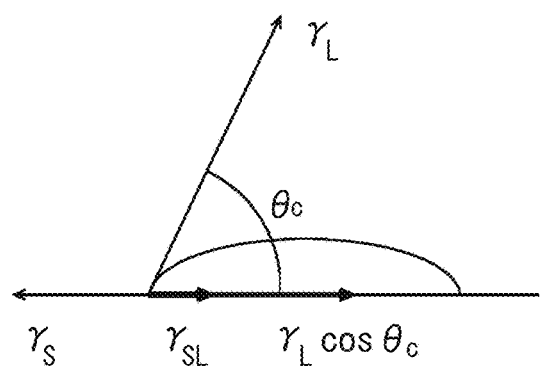
FIG. 6 is a drawing for explaining a contact angle between a material of wall surfaces and a culture medium.

FIG. 6 is a schematic diagram for explaining the contact angle θc between the quality of the material that appears on the wall surfaces 13 and the culture medium 8. The contact angle θc is a contact angle of a liquid with respect to a solid. The contact angle θc is determined by properties of the solid and liquid. Further, $\gamma_S$ is surface tension of the solid [g/cm], $\gamma_{SL}$ is solid liquid surface tension [g/cm], and $\gamma_L$ is surface tension of the liquid [g/cm].

The contact angle θc is determined by the properties of the solid and liquid. To be more specific, the contact angle θc is determined by quality of the material used for the spheroid-producing device 1 (quality of the material that appears on the wall surfaces 13) and the properties of the culture medium 8.

<Investigation on Contact Angle θc>

(1) The case when the contact angle θc is within a range of −1<cos θc≤0.

In this case, the size of the droplets is not influenced by the contact angle. An allowable range is an angle $\theta_0$=90 degrees.

When the contact angle θc is within a range of −1<cos θc≤0, the spheroid-producing device 1 is commonly regarded as being made of a hydrophobic material. In this regard, the diameters Din of the inscribed circles of the openings in the second surface 12 are smaller than the diameters of the inscribed circles of the openings in the first surface 11. In addition, the size of the equivalent diameter Dout of the circumscribed circles will become important.

Figure 5:
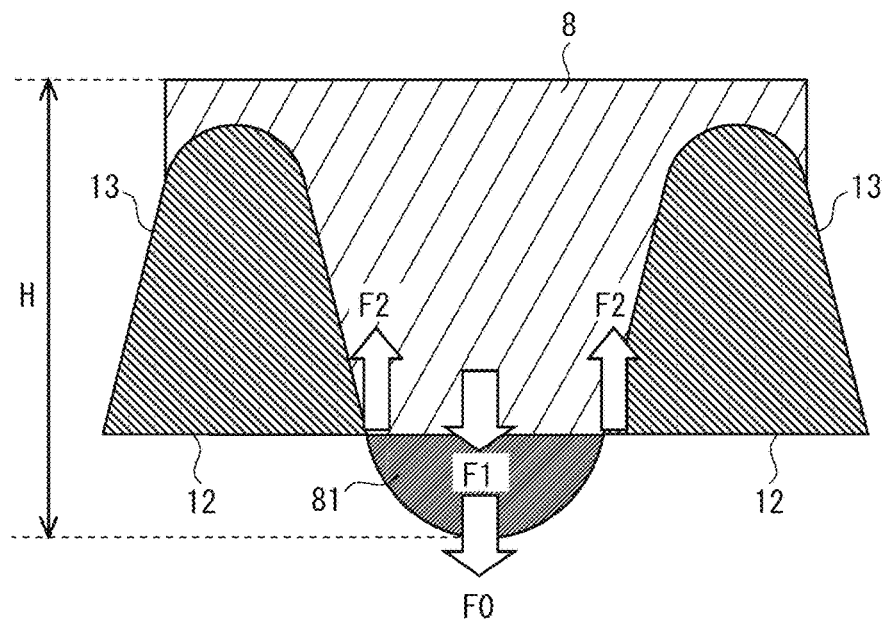
FIG. 5 is a drawing for explaining forces exerted on a droplet.

FIG. 5 is a drawing for explaining forces exerted on the droplet 81. In FIG. 5, the shape of the droplet 81 is considered to be hemispherical. The second surface is disposed to be horizontal. In practice, the droplet 81 is a liquid that is continuous with the culture medium 8 with no boundary between them. In FIG. 5, a range defined as being the droplet 81 is shaded differently from the culture medium 8 for easier descriptions.

F0 to F2 are present as the forces exerted on the droplet 81 and forces working in parallel to gravity.

F0 is a force of gravity exerted on the droplet 81 and calculated by the following equation.

$$F0 = \text{volume} \times \text{specific gravity} = V \cdot a$$

F1 is a force derived from a water pressure of the liquid (the culture medium 8) exerted on the droplet 81 and calculated by the following equation.

$$F1 = \text{water pressure} \times \text{area} = pS$$

In the case of an atmosphere pressure, $$F1 = \text{depth from upper liquid surface to droplet} \times \text{density of liquid} \times \text{area} = H\rho S$$

F2 is a force derived from surface tension of a liquid generated at a periphery of the liquid surface and calculated by the following equation.

$$F2 = \text{outer circumference} \times \text{liquid surface tension} \times \text{angle} = L\gamma_L \sin\theta_0$$

The surface tension of the liquid $\gamma_L$ can be measured by various methods such as the Wilhelmy method. Alternatively, the information can be obtained from the distributor. The contact angle θc can be measured by measuring the liquid (the culture medium and a buffer solution) and materials to be used using the droplet method and the gas-liquid method.

Figure 8:
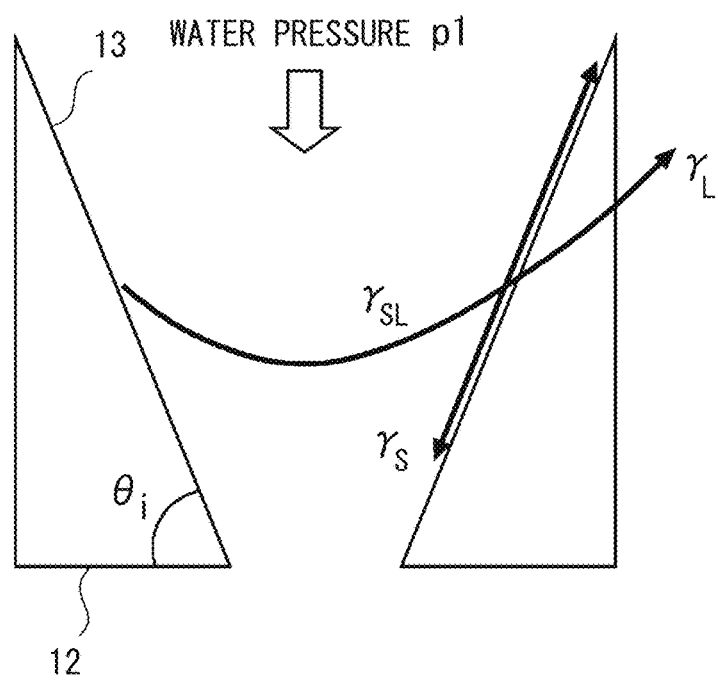
FIG. 8 is a drawing for explaining a relationship between a liquid surface and a water pressure.

In FIG. 8, $\gamma_{SL}$ is also related to a condition for a water surface to be stopped on the wall surface. On the other hand, $\gamma_{SL}$ is not related to a condition for droplets to be held as in FIG. 9. At this time, $\gamma_{SL}$ is assumed to be acting in a direction of the second surface.

In the above equations, a volume V is a volume [cm³] of the droplets 81, a specific gravity a is a specific gravity of the culture medium 8, a height H is a height equivalent to a depth [cm] from the upper surface of the culture medium 8 to a lower end of the droplet 81, and density p is density of the culture medium 8 [g/cm].

An area S is a size of an area of an opening at a position where the droplet 81 is generated (at a position where the droplet is formed in the hole). In this example, the area S is an area [cm²] of a boundary that is brought into contact with the second surface 12 and is the same as an area of the opening in the second surface 12.

Figure 7:
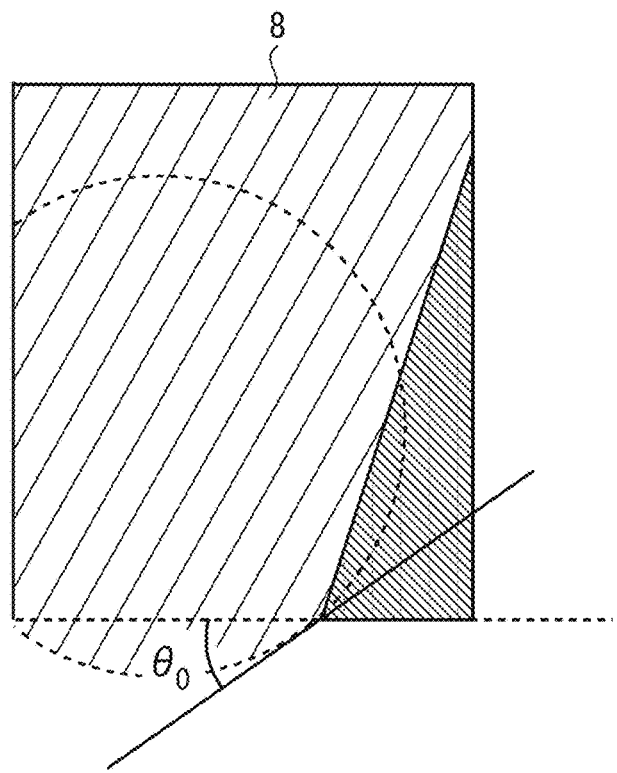
FIG. 7 is a drawing for explaining an angle $\theta_0$.

A water pressure p is a water pressure [g/cm²] at the opening in the second surface 12. A length L of an outer circumference is a length [cm] of a boundary at which the droplet is brought into contact with the second surface 12. The length L is equivalent to a length of a circumference of the opening in the second surface. The solid liquid surface tension $\gamma_{SL}$ is surface tension (interfacial tension) [g/cm] between the wall surfaces 13 and the culture medium 8. The angle $\theta_0$ is an angle the surface of the droplet 81 makes with a horizontal surface or the second surface 12 that is placed horizontally. When the droplet 81 is hemispherical in FIG. 5, the angle $\theta_0$=sin 90°=1. The angle $\theta_0$ is an angle a contact surface at a peripheral portion with which the droplet 81 is in contact makes with a horizontal surface. Alternatively, the angle $\theta_0$ is an angle this contact surface makes with respect to the second surface 12 that is placed horizontally. FIG. 7 is a drawing for explaining the angle $\theta_0$.

When the following equation 1 is satisfied, the droplets 81 are held in the spheroid producing device 1.

$$F0 + F1 < F2 \qquad \text{Equation 1}$$

When the droplets stay on the wall surfaces 13 as shown in FIG. 8, F2 can be expressed by the following equation from the above equation.

$$F2 = L\gamma_{SL} \sin\theta_t + L\gamma_L \sin\theta_0$$

(where $\theta_t$ is an inclined angle of the wall surfaces)

Thus, the equation 1 (F0+F1<F2) can be expressed by the following equation 2.

$$V\alpha + pS < L\gamma_{SL} \sin \theta_i + L\gamma_L \sin \theta_0 \quad \text{Equation 2}$$

Figure 9:
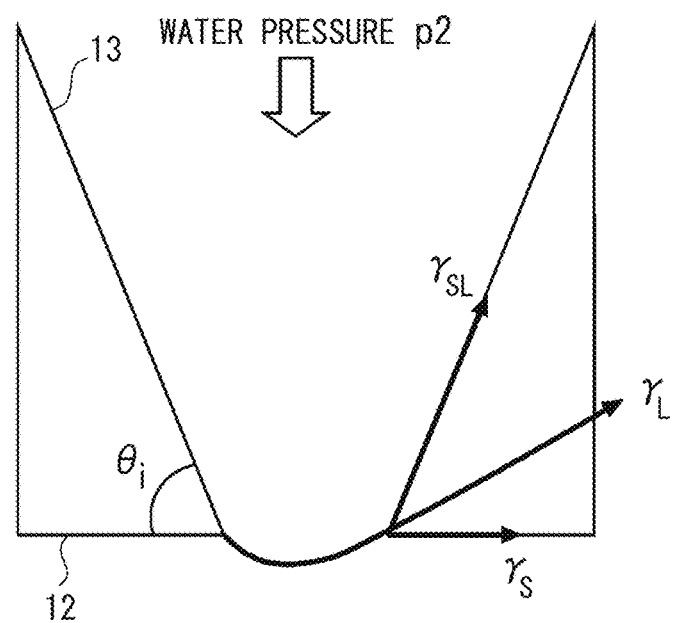
FIG. 9 is a drawing for explaining a relationship between a liquid surface and a water pressure when the water pressure is greater than that in FIG. 8.

Further, when the droplets are continuous with the second surface 12 as shown in FIG. 9, F2 can be expressed by the following equation.

$$F2 = L\gamma_L \sin \theta_0$$

Accordingly, the equation 1 (F0+F1<F2) can be expressed by the following equation 3.

$$V\alpha + pS < L\gamma_L \sin \theta_0 \quad \text{Equation 2-2}$$

Assume that the culture medium 8 is poured up to the height H using a material having the contact angle θc. When the droplets 81 start to become narrow, the droplets 81 start to project outwardly from the second surface 12. At this time, F0+F1=F2 is satisfied. The angle $\theta_0$ is 90 degrees (sin 90=1).

F0 can be expressed by the following equation, where V is a volume of the droplet 81, Rout is the equivalent radius of the circumscribed circle of the opening in the second surface 12, and α is the specific gravity.

$$F0 = ((4/3)\pi \text{Rout}^3 \div 2) \times \alpha = (2/3)\pi R^3 \cdot \alpha.$$

However, when the droplet 81 is hemispherical, the volume V is calculated by

[(volume of the sphere)÷2].

Further, the following equation is satisfied, when the area of the opening S and the length of the outer circumference L of the opening are expressed by an equivalent radius R.

$$S = \pi \text{Rout}^2, \quad L = 2\pi \text{Rout}$$

From the equation 3, $$(2/3)\pi \text{Rout}^3 \cdot \alpha + p\pi \text{Rout}^2 = 2\pi \text{Rout} L \gamma_L \sin 90$$

In this equation, sin 90=1.
Accordingly, $$(2/3)\alpha \text{Rout}^2 + p\text{Rout} = 2\gamma_L \quad \text{Equation 3}$$

That is, the equivalent diameter Rout of the circumscribed circle in the equation 3 is preferably a maximum equivalent radius of the openings in the second surface 12. The diameters of the openings in the second surface 12 are preferably 2Rout or less. It is more preferable to design the device in consideration of a force (Fc) exerted from gravity on cell aggregates.

As described above, when the contact angle θc is within a range of −1<cos θc<0 (the contact angle is 90 degrees or greater, and $\theta_0$ will not exceed θc), it is preferable that the equivalent diameter Dout of the circumscribed circles of the openings in the second surface 12 are less than or equal to twice the equivalent radius of the circumscribed circles calculated by the equation 3. With this exemplary embodiment, the droplets can be maintained in the spheroid-producing device 1.

(2) The case when the contact angle θc is within the range of 0<cos θc<1

When the contact angle θc is within the range of 0<cos θc<1, the spheroid-producing device 1 is commonly regarded as being made of a hydrophilic material. The equivalent diameter of the inscribed circles are used in designing the size of the openings 12 in the second surface when such a material is used.

Figure 10:
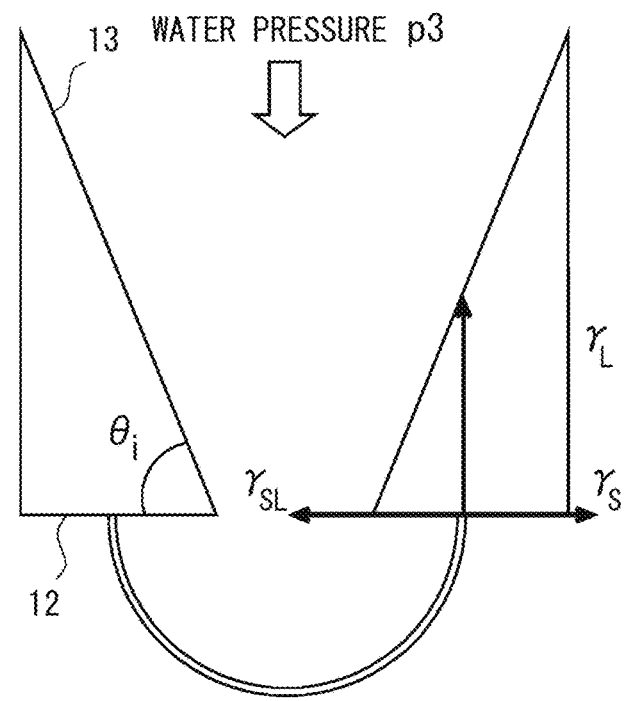
FIG. 10 is a drawing for explaining a relationship between a liquid surface and a water pressure when the water pressure is greater than those in FIGS. 8 and 9.

A relationship between the liquid surface and water pressure will be described with reference to FIGS. 8 and 9. When a water pressure p1 in FIG. 8 is used as a reference, FIG. 9 shows a case in which a water pressure p2 is greater than the water pressure p1 of FIG. 8 (p1<p2). FIG. 10 shows a case in which a water pressure is greater than the water pressures in FIGS. 8 and 9 (p1<p2<p3). FIG. 8 shows a state in which the magnitude of the water pressure p1 and the liquid surface are balanced, and in which the liquid will not fall down and is stopped. FIG. 9 shows a state in which the liquid surface is closer to the second surface 12 as compared to the state in FIG. 8 because the water pressure p2 is greater than the water pressure p1. In FIG. 9, the magnitude of the water pressure P2 and the liquid surface are balanced. The greater the height H in FIG. 5 (the more the amount of the culture medium 8), the greater the water pressure becomes. As a result, when $\theta_0$ exceeds the contact angle $\theta_c$, a triple line at which the liquid, the device, and air are brought into contact with one another moves as shown in FIG. 10. Thus, the liquid surface comes around the openings in the second surface 12 and is adhered to the second surface 12. In the state shown in FIG. 10, the liquid is continuously supplied from above the spheroid-producing device 1. As a result, the droplets are enlarged and drop, thereby making it difficult to stably hold one droplet in each hole. That is, the state shown in FIG. 8 or 9 is preferable.

Figure 11:
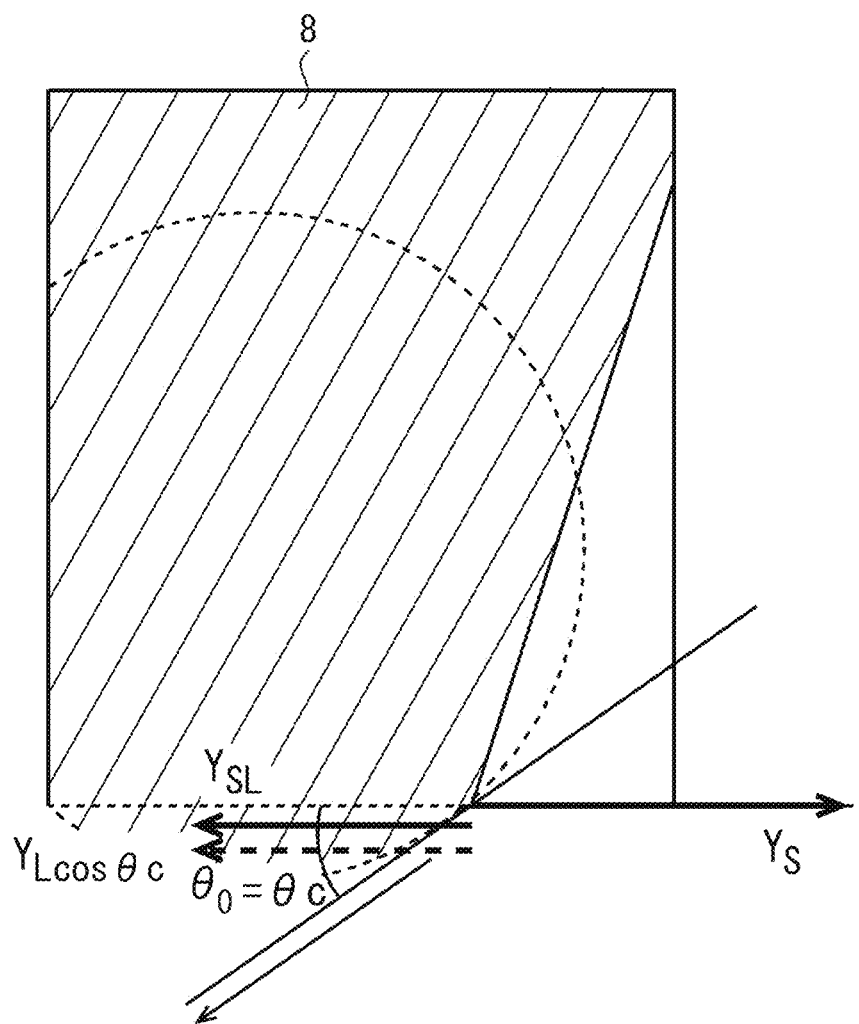
FIG. 11 is a drawing for explaining surface tension of openings in a second surface when the liquid surface and the water pressure are balanced.
Figure 12:
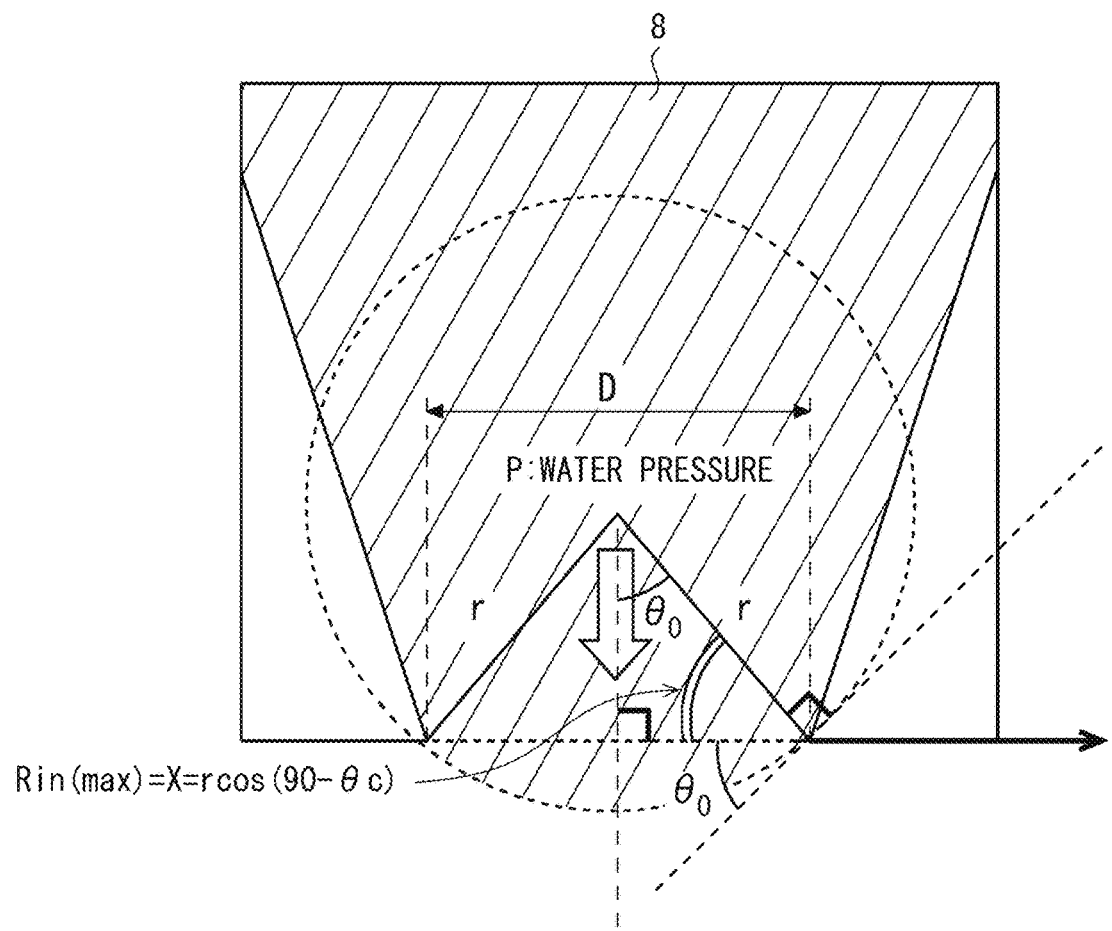
FIG. 12 is a drawing for explaining surface tension of openings in the second surface when gas and the water pressure are balanced.

Therefore, it is preferable to design the spheroid-producing device 1 so that the following conditions are satisfied. FIG. 12 is a drawing for explaining surface tension at the opening in the second surface 12 when the liquid surface and the water pressure are balanced. FIG. 11 shows a case when the surface tension is adjusted to achieve the state of FIG. 9.

A condition for avoiding the state of FIG. 10 is that the surface tension of the solid $\gamma_S$ does not exceed a sum of the solid liquid interfacial tension $\gamma_{SL}$ and the surface tension of the liquid surface ($\gamma_L \cos \theta_0$).
That is, $$\gamma_S \leq \gamma_{SL} + \gamma_L \cos \theta_0 \quad \text{Equation 5}$$

In comparison between the equation 5 and the Young equation ($\gamma_S = \gamma_{SL} + \gamma_L \cos \theta_c$), when $\theta_0 \leq \theta_c$ is satisfied, droplets are stably maintained.

FIG. 6 is a schematic diagram for explaining the contact angle θc between the material of the wall surfaces 13 and the culture medium 8. The contact angle θc is a contact angle of the liquid with respect to the solid and determined by properties of the solid and liquid. In the equations, $\gamma_S$ is the surface tension of the solid [g/cm], $\gamma_{SL}$ is the solid liquid surface tension [g/cm], and $\gamma_L$ is the surface tension of the liquid [g/cm].

The contact angle θc is determined by the properties of the solid and liquid, and more specifically, determined by the materials (the materials of the second surface 12 and the wall surfaces 13) of the spheroid-producing device 1 and the properties of the culture medium 8.

The surface tension $\gamma_{SL}$ of the solid is preferably obtained on the Internet (http://www.surface-tension.de/solid-surface-energy.htm) or obtained from a distributor etc. Alternatively, the surface tension $\gamma_{SL}$ of the solid may be calculated using the Zisman method. The surface tension of the liquid $\gamma_L$ can be measured by various methods such as the Wilhelmy method. Alternatively, the information can be obtained from a distributor. The contact angle θc can be measured by measuring the liquid (the culture medium and a buffer solution) and materials to be used using the droplet method and the gas-liquid method. Thus, $\gamma_{SL}$ can be derived by substituting the values of $\gamma_L$ and $\gamma_S$ into the equation of $\gamma_{SL} = \gamma_L \cos \theta c - \gamma_S$.
Therefore, the equation 5 is;

$$\gamma_S \leq \gamma_L \cos \theta c - \gamma_S + \gamma_L \cos \theta c$$

$$\gamma_L \cos \theta c - \gamma_S \geq 0 \quad \text{Equation 6}$$

As shown in FIG. 12, as to the downward liquid surface of the droplets 81, a pressure difference ΔP(P-Pair) between air and liquid surrounding the droplets in accordance with the Young-Laplace equation can be expressed as:

$$\Delta P = p = \gamma L(1/r1 + 1/r2) \quad \text{Equation 7}$$

In the case of an atmospheric pressure, it is expressed by the following equation.

$$\Delta P = H\rho = \gamma L(1/r1 - 1/r2) \quad \text{Equation 7-2}$$

The droplets have curved surfaces and project downwardly. $\gamma_L$ this equation, $\gamma_L$ is the surface tension of the liquid [g/cm], and r1 [cm] and r2 [cm] are radii of curvature that are orthogonal to each other at one point on the surface, When the surfaces of the droplets 81 are spherical, r1=r2 is satisfied.
Thus, $$p = \gamma L \times (2/r) \quad \text{Equation 8}$$

In the case of an atmospheric pressure, it is expressed by the following equation.

$$H\rho = \gamma L \times (2/r) \quad \text{Equation 8-2}$$

As described above, from the moment when the droplets flow over the second surface 12, it will be difficult to hold the droplet. In view of the above, with the contact angle θc that is within a range of 0<cos θc<1, a relationship between conditions when $\theta_0 = \theta_c$ and the equivalent diameter Din of the inscribed circles of the openings in the second surface 12 will be examined with reference to FIG. 12.

When the culture medium with properties of ρ and $\gamma_L$ is poured up to the height H [cm] using a material with a property of $\gamma_S$ under an atmospheric pressure, a material that satisfies cos θc>$\gamma_S$/$\gamma_L$, which is derived from the equation 6, is selected.

A vertical auxiliary line is drawn down from a center of a circle that is estimated from the radius of curvature, the following equation is satisfied.

$$Din = 2r \cdot \sin \theta_0$$

From the equation 8-2, as r=2HργL it can be expressed by the following equation.

$$Din = 4 \cdot \gamma L \cdot \sin \theta_0 / H\rho \quad \text{Equation 9}$$

When a limit at which the droplets can flow over the second surface 12, which is when $\theta_0 = 0$, is substituted into the above equation, a maximum diameter Din (max) of the inscribed circles that can hold the droplets is expressed by the following equation.

$$Din(max) = 4 \cdot \gamma L \cdot \sin \theta_c / H\rho \quad \text{Equation 9-2}$$

That is, it is preferable to design the device in such a way that the diameters of the inscribed circles will be smaller than the value calculated by the above formula.

When the device is designed under such conditions, regardless of the contact angle θc (i.e., whether the material of the device is hydrophobic or hydrophilic), it is preferable to consider absorption of protein contained the culture medium into the material when the device is designed. It is thus preferable that the size of the openings in the second surface 12 is a value within a range of 20 to 80% of a maximum value of the calculated equivalent radius R. Further, it is preferable to adjust the height H of the culture medium 8 in such a way that a water pressure derived from the height H of the culture medium 8 will be within a range of 50 to 80% of the calculated maximum water pressure p in order to adjust the amount of the culture medium.

As described above, it is possible to manufacture the spheroid-producing device 1 in which droplets are appropriately formed by designing the equivalent diameter Din of the inscribed circles and the equivalent diameter Dout of the circumscribed circles according to the contact angle θc. In other words, it is possible to design and produce the spheroid-producing device 1 according to the material used for the spheroid-producing device 1 and the properties of the culture medium 8 used for cell culture. As the droplets suitable for cell culture can be formed by the spheroid-producing device 1, it is expected that a large number of spheroids can be efficiently produced using the spheroid-producing device 1. In addition, it is expected that uniform spheroids be produced by forming appropriate droplets using the spheroid-producing device 1.

Note that in the above (1) to (3), the equations used to design the spheroid-producing device 1 according to the range in which the value of the contact angle θc can be included have been presented. This is because it is preferable to test several design methods according to the material of the spheroid-producing device 1 or the properties of the culture medium 8. Further, this is because the spheroid-producing device 1 is designed and manufactured using preferable equation(s) as appropriate.

<Width of Upper Surface>

A width W of the upper surface of a wall that partitions spaces is preferably 5 mm or less. More preferably, the width W is 2 mm or less so that cells will not stay or stand still on the upper surface (on the first surface 11 and near the first surface 11). It is preferable to consider a shape of the upper surface (a shape of an upper portion from the first surface 11 to the width of the upper surface) together with the width W of the upper surface. This will be described later in detail with reference to FIGS. 17 to 22.

<Material of Spheroid-Producing Device>

The spheroid-producing device 1 is preferably a resin molding made of one of or a combination of acrylic resin, polylactic acid, polyglycolic acid, styrene resin, acrylic-styrene copolymer resin, polycarbonate resin, polyester resin, polyvinyl alcohol resin, ethylene-vinyl alcohol copolymer resin, thermoplastic elastomer vinyl chloride resin, silicone resin, and silicon resin. This is because resin that can be molded is used in order to manufacture devices at a low cost and in large numbers.

Further, when the spheroid-producing device 1 is the above-mentioned resin molding, it is preferable to form functional groups at least on the wall surfaces 13 by the surface modification treatment, which is one of or a combination of plasma treatment, corona discharge, and UV ozone treatment. Functional groups may be formed on the entire spheroid-producing device 1. This is because when the device is too hydrophobic or when the openings are too small, providing the device with a hydrophilic property enables a culture medium to be smoothly poured into the openings.

Furthermore, when the spheroid-producing device 1 is the above-mentioned resin molding, it is preferable that at least the wall surfaces 13 are coated with a substance made of one of or a combination of inorganic substances, metal, synthetic polymers, dimers, trimers, tetramers, and biobased polymers. Alternatively, the entire spheroid-producing device 1 may be coated with these substances. The reason for this is the same as the one described above. Additionally, it is extremely effective to coat the surface with the above material(s) and to thereby form a hydrophobic surface. This is because when a culture medium having low surface tension is used, a hydrophobic surface of the device is more effective than a hydrophilic surface of the device, provided that both of the devices have holes with the same equivalent diameter.

Moreover, it is preferable that the spheroid-producing device 1 is a molding made of one of or a combination of inorganic substances such as metal and glass. When the spheroid-producing device 1 is the above-mentioned molding, it is preferable to modify at least the wall surfaces 13 by the surface modification treatment, which includes one of or a combination of plasma treatment, corona discharge, and UV ozone treatment. The entire surface of the spheroid-producing device 1 may be modified. The reason for this is the same as the one described above. Additionally, it is extremely effective to create a more hydrophobic surface by coating the surface with the above-mentioned material. This is because when a culture medium having low surface tension is used, a hydrophobic surface of the device is more effective than a hydrophilic surface of the device, provided that both of the devices have holes with the same equivalent diameter.

Alternatively, when the spheroid-producing device 1 is the above-mentioned molding, at least the wall surfaces 13 are coated with a substance made of one of or a combination of inorganic substances, metal, polymer, diners, trimers, and tetramers. The entire spheroid-producing device 1 may be coated with these substances. The reason for this is the same as the one described above. Additionally, it is extremely effective to create a more hydrophobic surface by coating the surface with the above-mentioned material. This is because when a culture medium having low surface tension is used, a hydrophobic surface of the device is more effective than a hydrophilic surface of the device, provided that both of the devices have holes with the same equivalent diameter.

In addition to the above processing, at least the front surfaces of the wall surfaces 13 or the entire spheroid-producing device 1 preferably includes nanometer order microstructures. The microstructures are, for example, structures with their front surfaces processed to have uneven surfaces. Properties of the material front surface are not specified by the material of the device but are specified by the properties of the material front surface. As hydrophilicity/hydrophobicity of the front surface of the material can be controlled in aftertreatment, any material may be used as a material for the device.

<Method for Recovering Spheroids>

An outline of a method for producing spheroids using the above-mentioned spheroid-producing device 1 and a method for recovering the produced spheroids will be described below.

Figure 13:
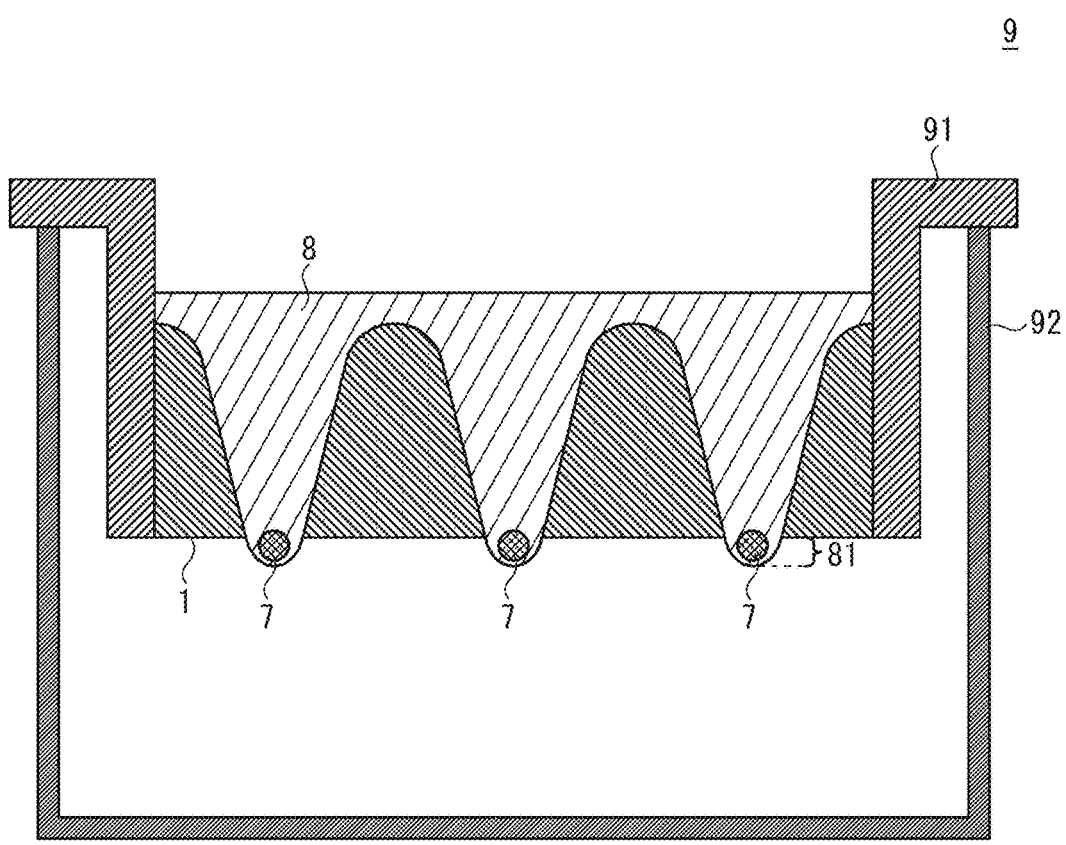
FIG. 13 is a drawing for explaining a process for producing spheroids.

FIG. 13 is a drawing for explaining processes for producing spheroids using the cell culture container 9 shown in FIG. 4. The culture medium 8 containing cells is poured into respective holes in the spheroid-producing device 1 from the side of the first surface 11. If the spheroid-producing device 1 is designed appropriately as described above, the culture medium 8 projects from a bottom of the spheroid-producing device 1 (the openings in the second surface), thereby forming droplets of the culture medium. The cells contained in the culture medium 8 are aggregated in the droplet portions and form spheroids 7. During cell culture, for example, a supernatant of the culture medium 8 is extracted, and the culture medium 8 is exchanged with a new culture medium by being supplemented with the new culture medium.

FIG. 4 is a drawing for explaining another example of processes for producing spheroids using the cell culture container 9 shown in FIG. 4. FIG. 14 is a drawing showing a state in which droplets do not reach openings in the second surface 12 and are stopped halfway down the openings. Such a phenomenon occurs when a culture medium is added up to a height lower than the height H, which has been designed, into the spheroid-producing device 1 that is appropriately designed as described above. Even in such a case, cells contained in the culture medium 8 are aggregated in the droplet portions to form the spheroids 7. During cell culture, for example, a supernatant of the culture medium 8 is extracted, and the culture medium 8 can be exchanged with a new culture medium by being supplemented with the new culture medium. In order to recover spheroids, the culture medium is added from the side of the first surface 11 so as to increase H or a pressure on the side of the first surface is increased, so that the state shown in FIG. 14 is achieved, and then spheroids can be recovered by the method shown in FIG. 15 or 16.

The produced spheroids 7 are recovered by, for example, the methods shown in FIGS. 15 and 16, The spheroids 7 can be recovered without damaging the spheroids 7 by the methods described below.

Figure 15:
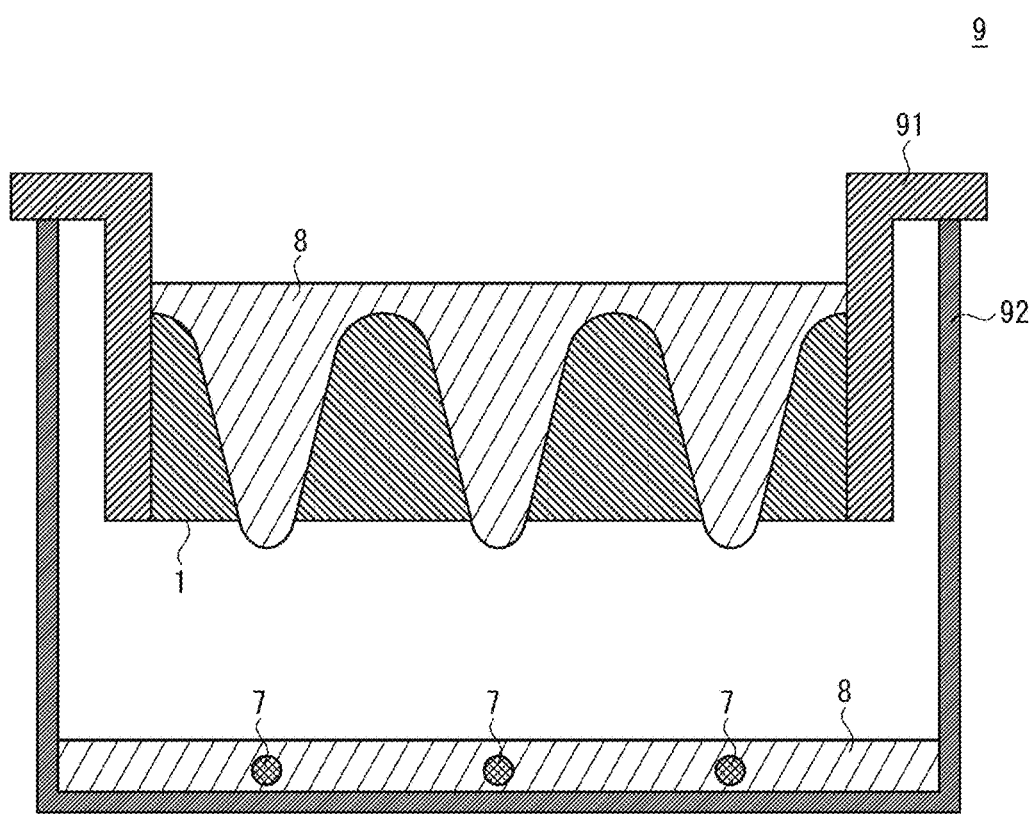
FIG. 15 is a drawing for explaining a method for recovering spheroids (using a culture medium)

FIG. 15 shows a method for recovering the spheroids 7 by placing a recovery solution in the Petri-dish 92 and bringing the recovery solution into contact with the second spheroids 7, The recovery solution can be selected from any one of, for example, the culture medium 8, water, and a buffer solution. The spheroids 7 that are produced by culturing the cells using the spheroid-producing device 1 are extracted by this method. A preferred exemplary embodiment of this method is collecting the spheroids by moving the droplets to a side of the recovery solution. It is particularly preferable to bring the droplets formed on the side of the second surface 12 into the recovery solution when the droplets are moved.

Figure 16:
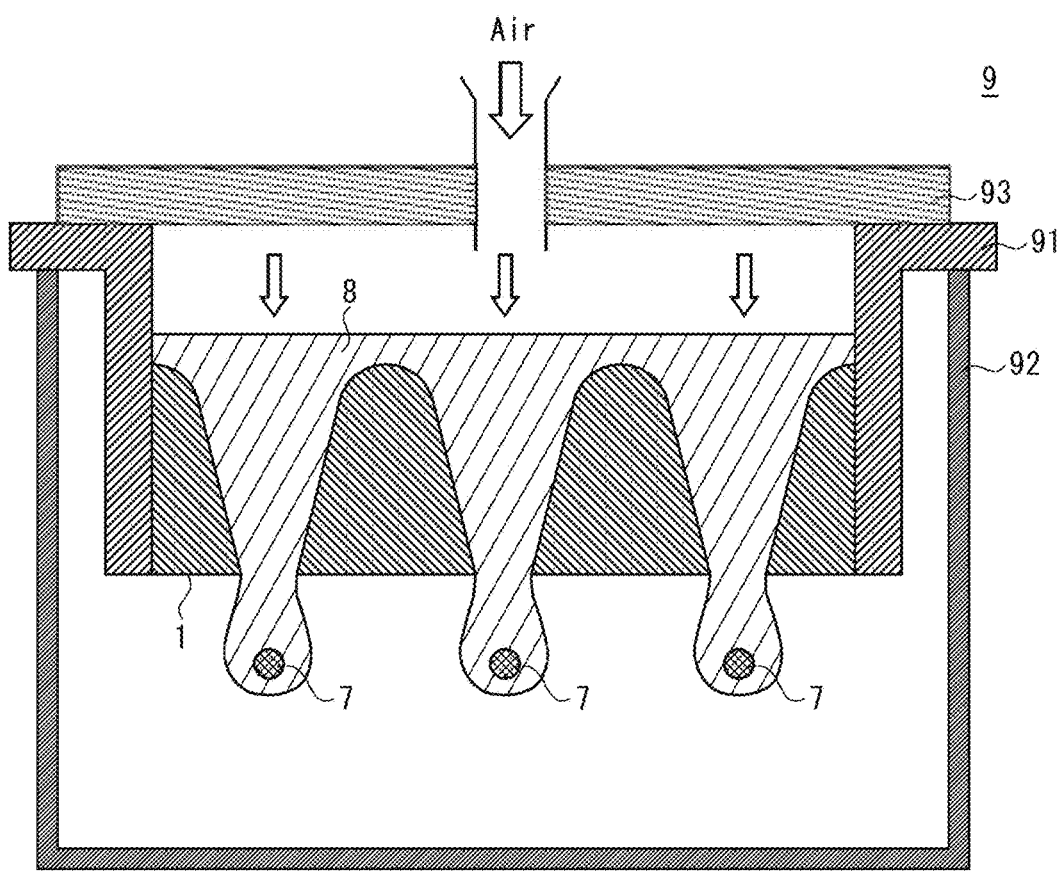
FIG. 16 is a drawing for explaining another method for recovering spheroids (by a pressure)

FIG. 16 shows a method for recovering the spheroids 7 by applying a pressure from the side of the first surface 11 while the cell culture container 9 is closed with a lid 93. When a pressure is applied from the side of the first surface 11, the droplets are destroyed. As a result, the culture medium 8 flows out in the Petri-dish 92 to thereby enable the spheroids 7 to be recovered. It is preferable to destroy the droplets in a manner described above when spheroids cultured using the spheroid-producing device 1 are extracted. Any method may be used to apply a pressure from the side of the first surface 11 in order to destroy the droplets. For example, the culture medium 8 may be added until the droplets are destroyed. Alternatively, the side of the first surface 11 is sealed and gas is supplied in order to apply a pressure.

As described above, with the spheroid-producing device 1 according to this exemplary embodiment, it is possible to generate droplets in a plurality of holes and to produce spheroids. It is thus possible to efficiently produce a large number of spheroids. When the size of the plurality of holes is formed to be the same, uniform spheroids can be produced. In addition, a culture medium can be poured from the side of the first surface 11 (the upper side) into the spheroid-producing device 1. Further, the culture medium can be exchanged from the side of the first surface 11. Accordingly, an operation of the spheroid-producing device 1 is easy. Furthermore, a structure of the spheroid-producing device 1 can be simple by designing the spheroid-producing device 1 based on the physical phenomenon. It is thus possible to easily manufacture the spheroid-producing device 1 itself compared to the suspension plate disclosed in patent literature 2. Consequently, it is possible to greatly reduce a cost and a working time for producing spheroids.

Second Exemplary Embodiment

Figure 20:
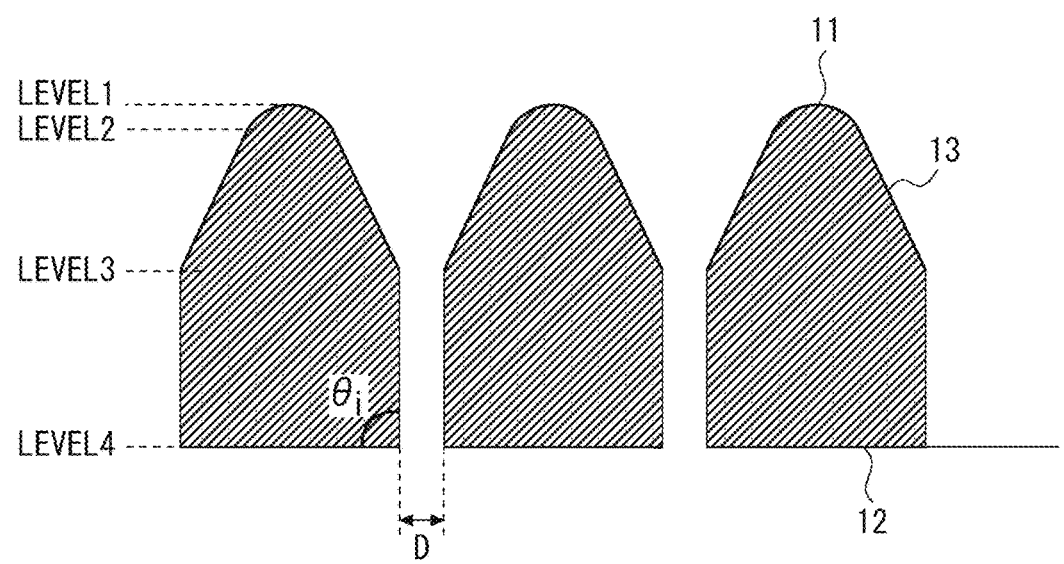
FIG. 20 is a drawing showing another example of the cross-sectional shape of the spheroid-producing device.

In the first exemplary embodiment, although the spheroid-producing device 1 having shapes of the holes shown in FIGS. 1 and 2 has been described, the shapes of the holes are not limited to them. For example, the spheroid-producing device 1a to 1f having cross sections shown in FIGS. 17 to 22, respectively, instead of the cross section shown in FIG. 2, may be employed. In a manner similar to the device shown in FIG. 2, the devices for producing spheroids 1a to 1c are examples in which the wall surfaces 13 are formed from boundaries with the second surfaces 12 with inclined surfaces having the angle θi. On the other hand, the spheroid-producing device 1d shown in FIG. 20 is an example in which the inclined surfaces with the angle start halfway on the wall surfaces 13.

Figure 17:
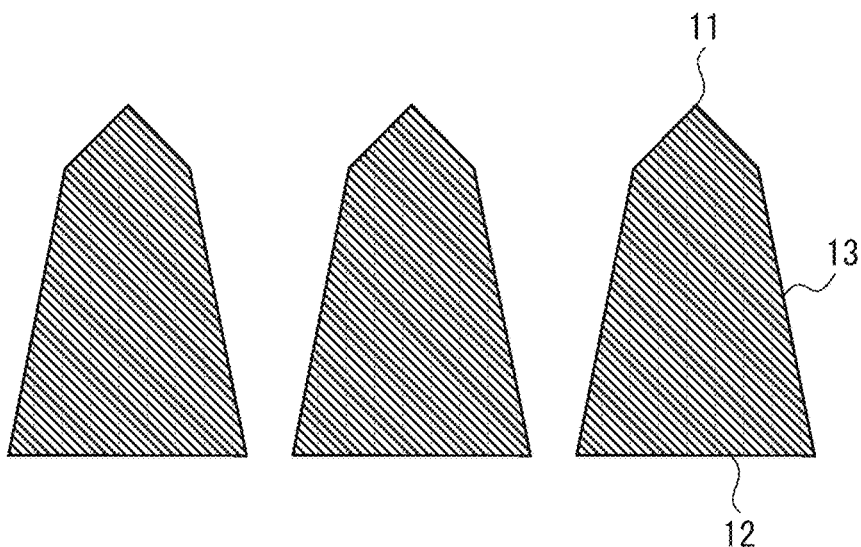
FIG. 17 is a drawing showing an example of a cross-sectional shape of the spheroid-producing device.
Figure 18:
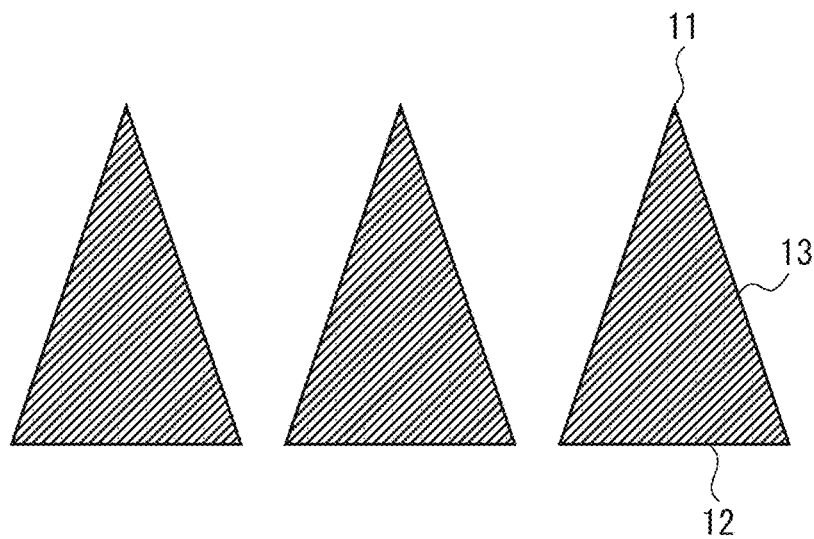
FIG. 18 is a drawing showing another example of the cross-sectional shape of the spheroid-producing device.
Figure 19:
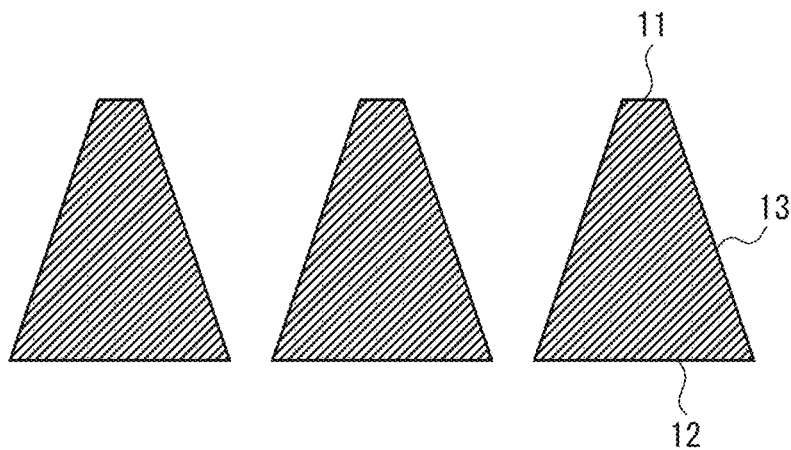
FIG. 19 is a drawing showing another example of the cross-sectional shape of the spheroid-producing device.

The shapes of the upper surfaces may be, as shown in the examples of FIGS. 2 and 17 to 22, portions of spheres (FIGS. 2 and 20 to 22), respectively, or flat (FIG. 19), Alternatively, the shapes of the upper surfaces may be cones or polygonal cones having vertexes (FIGS. 17 and 18). In one exemplary embodiment of the spheroid-producing device, more preferably, the shapes of the upper surfaces are round or are cones or polygonal cones having vertexes in order to prevent cells from staying or standing still on the upper surfaces. In addition, the shapes of the upper surfaces may be vertical from the openings in the first surface 11 to entries of the holes and have inclined portions only near the openings in the second surface 12, which are not shown in the drawings.

Figure 21:
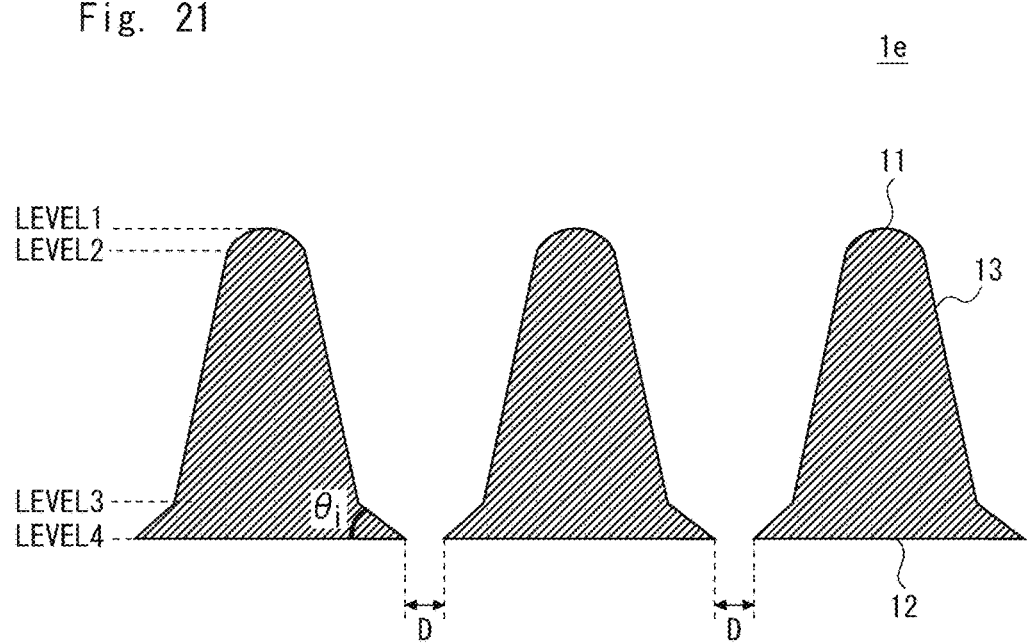
FIG. 21 is a drawing showing another example of the cross-sectional shape of the spheroid-producing device.

The spheroid-producing device 1d shown in FIGS. 20 to 22 will be described below. The equivalent diameter D and the angle θi are an equivalent diameter and an angle, respectively, at the position where the device is brought into contact with the culture medium at the opening in the second surface 12 of the device. The shape of the device may be those shown in FIGS. 20, 21, and 22. FIG. 20 is a drawing showing a case in which the wall surfaces 13 from the level 2 to 3 have angles. In FIG. 20, the equivalent diameter of the inscribed circles of the openings at the level 3 is the same as the equivalent diameter of the inscribed circles at the level 4. In this case, the position at the level 4 is a reference for the equivalent diameter Din of the inscribed circles and the angle θi. FIG. 21 is a drawing showing an example in which the wall surfaces 13 from the level 3 to 4 have angles. In FIG. 21, the equivalent diameter of the inscribed circles of the opening at the level 3 is greater than the equivalent diameter D of the inscribed circles at the level 4. In this case, the position at the level 4 is a reference for the equivalent diameter Din and the angle θi of the inscribed circles. At this time, inclinations of the wall surfaces 13 from the level 3 to 4, namely the angle θi, are preferably smaller than inclinations of the wall surfaces 13 from the level 2 to 3.

Figure 22:
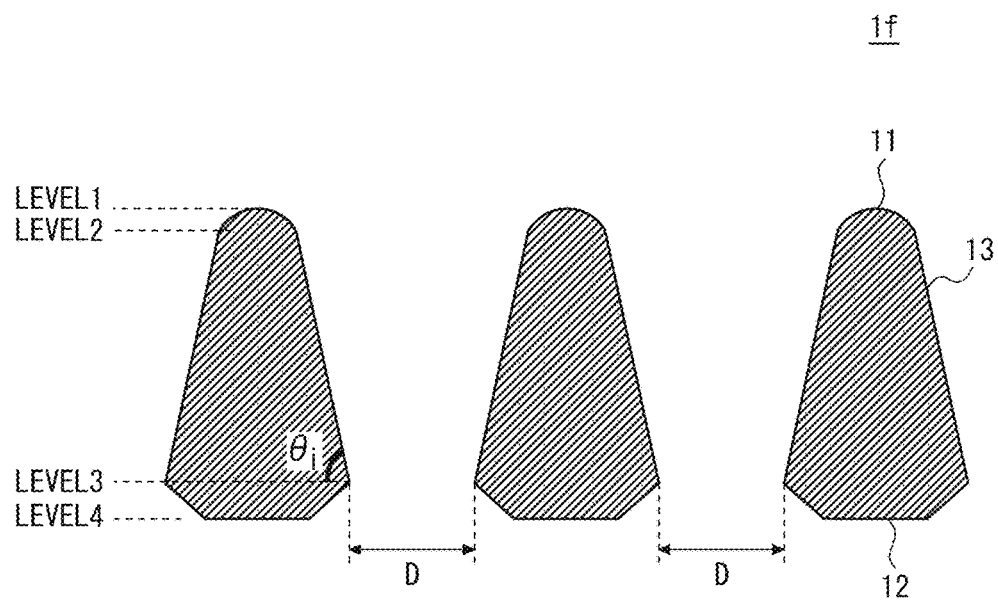
FIG. 22 is a drawing showing another example of the cross-sectional shape of the spheroid-producing device.

Alternatively, as shown in FIG. 22, the wall surfaces 13 from the level 2 to 3 may have angles. In this case, the equivalent diameter of the inscribed circles of the opening at the level 4 is greater than the equivalent diameter of the inscribed circles of the opening at the level 3. At this time, the lowest level at which the wall surfaces 13 are brought into contact with the culture medium is the level 3. Therefore, inclinations from the level 2 to 3 have the angle θi, and the positions at the level 3 are the equivalent diameter Din of the inscribed circles. In FIGS. 20 to 22, the angles θi are angles at the part of openings in the second surface (the lower surface) or the side of the second surface wherein the part contacts with the liquid surface.

In the first exemplary embodiment, cases in which the openings formed in the first surface 11 and the second surface 12 shown in FIGS. 1 and 2 are circular have been explained. However, the shapes of the openings are not limited to this. For example, devices for producing spheroids 1g to 1j with openings having shapes shown in FIGS. 23 to 26, respectively, may be employed. As has been described with reference to FIGS. 1 and 2, the spheroid-producing device 1 preferably includes the first surface 11 (the upper surface), the openings in the first surface 11, and the openings in the second surface 12 (the lower surface) as portions that are brought into contact with the culture medium. Further, the equivalent diameter of the inscribed circles of the openings in the first surface 11 is preferably greater than the equivalent diameter Din of the inscribed circles of the openings in the second surface 12. Thus, the shapes of the holes may be, as indicated by the devices for producing spheroids 1g to 1j, circles or polygons such as rectangles or octagons. Further, the shapes of the openings in the first surface 11 may differ from the shapes of the opening in the second surface 12. In FIGS. 23 to 26, the openings in the first surfaces 11 (or the shapes of the openings at the position of the width W of the upper surface) are denoted by solid lines. The openings in the second surfaces are denoted by dotted lines. These openings are shown as four holes when the devices for producing spheroids 1g to 1j are viewed from the side of the first surfaces 11.

In addition, in one exemplary embodiment of the spheroid-producing device, for example, holes may be created by punching a thin sheet-like film or a mold may be created, into which resin is poured, and then the resin may be molded into the device. In this regard, the equivalent diameter of the inscribed circles of the openings in the upper surface is made to be greater than the equivalent diameter Din of the inscribed circle of the openings in the lower surface. Moreover, a support(s) for reinforcing the film or resin may be included in order to support the weight of the culture medium. When the thickness of the film or resin is increased, the device may be hollowed out in order to reduce the weight of the device.

Example

A test for producing spheroids was carried out. Firstly, a spheroid-producing device 1x having the shapes shown in FIGS. 27 and 28 was designed and manufactured. Next, the spheroid-producing device 1x was attached to a well container 91x shown in FIGS. 29 and 30. The well container 91x shown in FIGS. 29 and 30 including the spheroid-producing device 1x was attached to a 6-well plate (not shown). At this time, it was confirmed that droplets 81 and the second surface 12 are not in contact with a bottom of the well plate.

Figure 27:
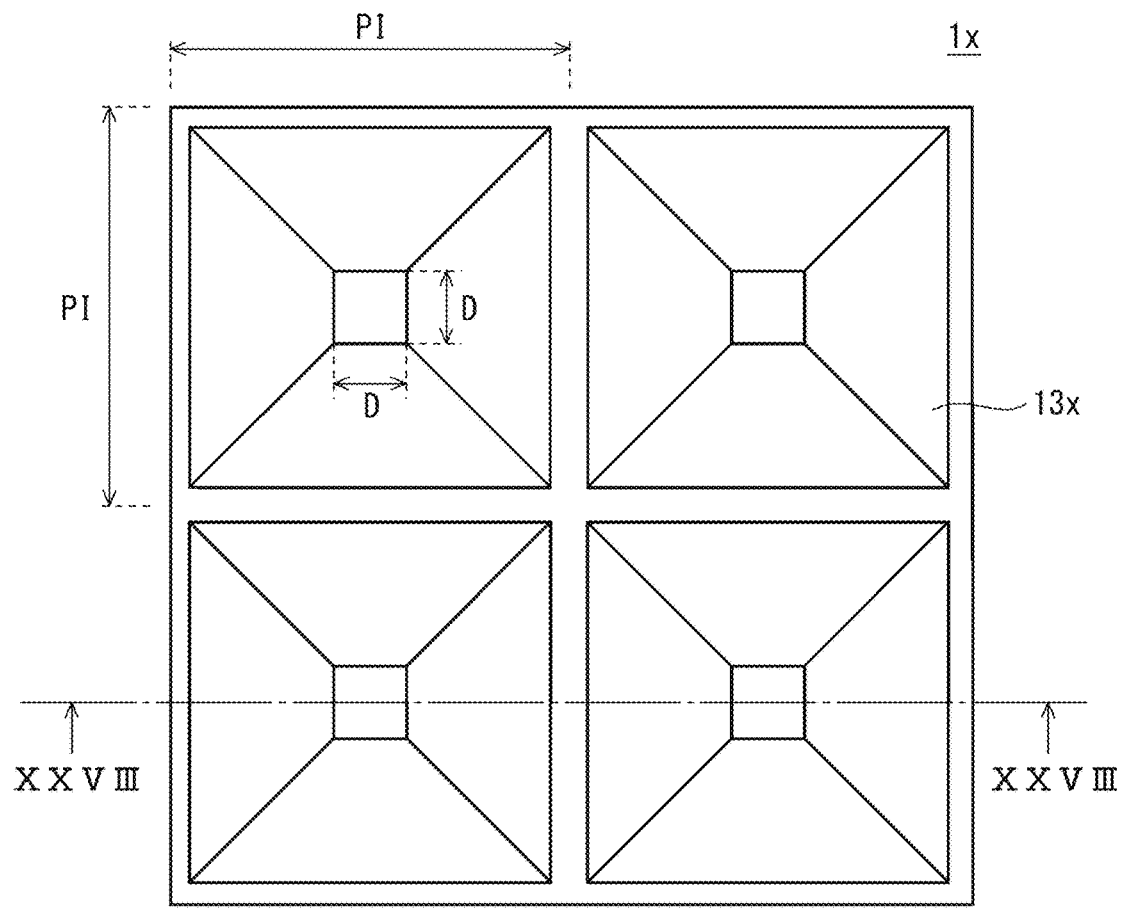
FIG. 27 is a drawing for explaining a shape of a spheroid-producing device used in an example.
Figure 28:
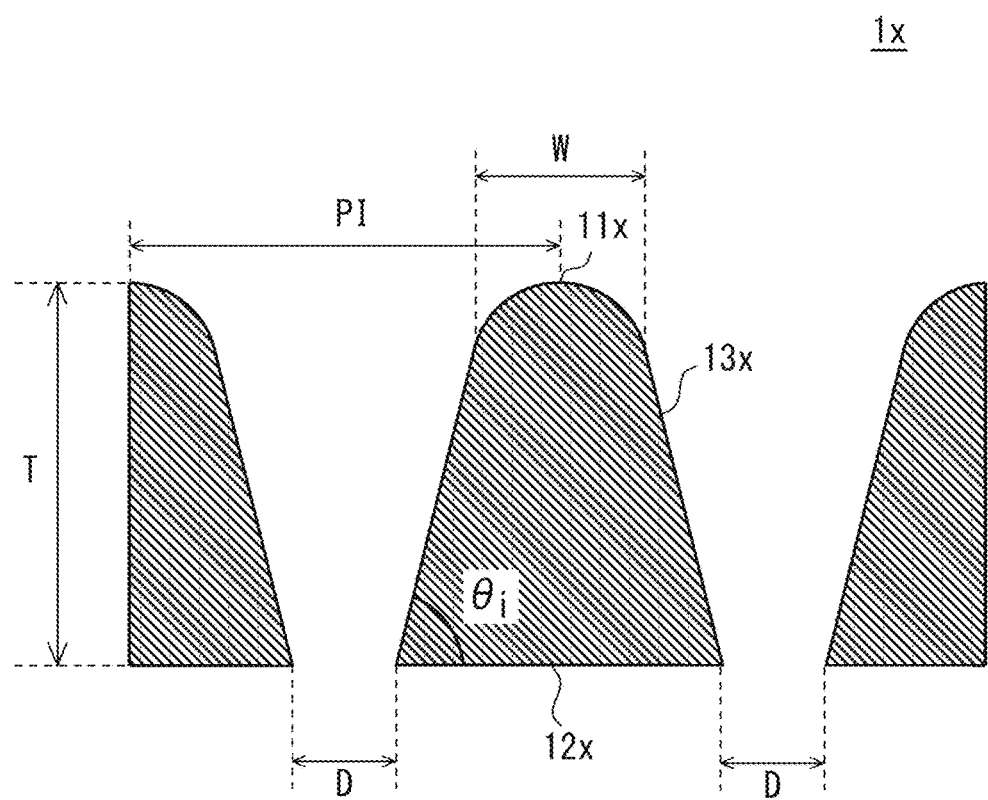
FIG. 28 is a cross-sectional diagram taken along the line XXVIII-XXVIII of FIG. 27.
Figure 29:
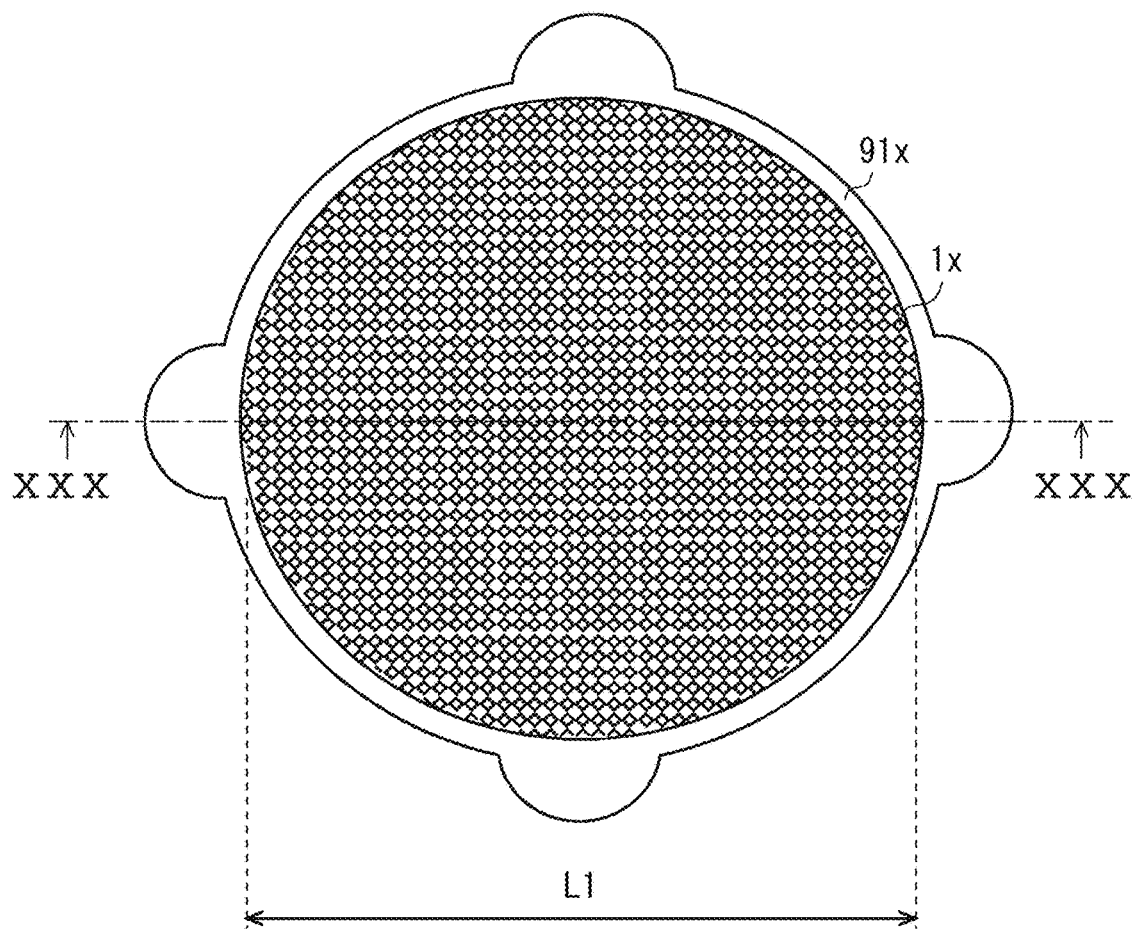
FIG. 29 is a drawing for explaining a configuration of a cell culture container used in the example.
Figure 30:
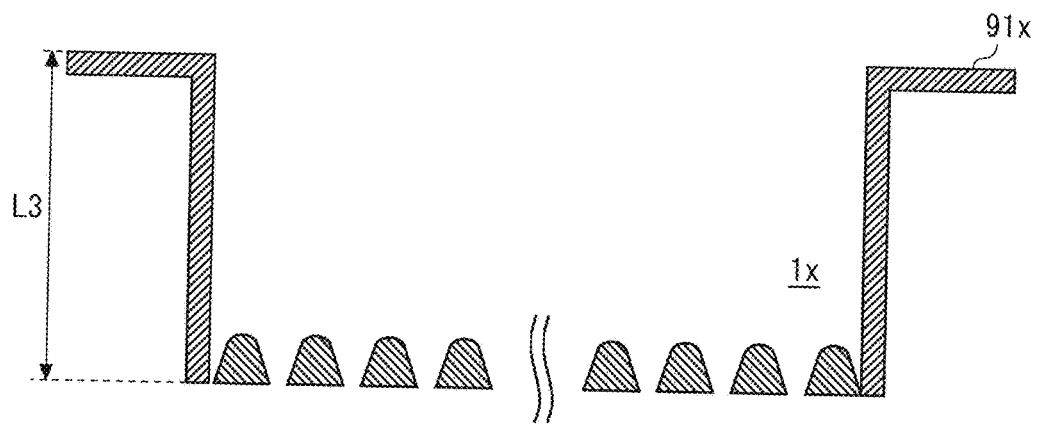
FIG. 30 is a cross-sectional diagram taken along the line XXX-XXX of FIG. 29.

FIG. 27 is a drawing showing the device when it is viewed from the first surface. FIG. 28 is a cross-sectional diagram taken along the line XXVIII-XXVIII of FIG. 27. FIG. 29 is a drawing of the device when it is viewed from the first surface. FIG. 30 is a cross-sectional diagram taken along the line XXX-XXX of FIG. 29.

The spheroid-producing device 1x was manufactured with the following size in which one pitch PI is 1.00 mm.
Equivalent diameter D of second surface 12x: 0.25 mm.
Angle θi: 67.5 degrees
Thickness T: 0.74 mm
Width W of upper surface: 0,184 mm
The size of the well container 91x is shown below.
Diameter of inner circumference of well container L1: 31 mm
Height of well container L3: 1.5 cm 1. Culture Container Example 1

A material having a contact angle θc within a range of $-1 < \cos \theta c < 0$ was used. Silicone (manufacturer: KCC and grade: SL7260) was used as a material for the spheroid-producing device. As the culture medium, 10% FBS added DMEM/F12 was used. Hereinafter, the culture medium will be referred to as a culture medium A.

<Design of Spheroid-Producing Device>

The above-mentioned equation 3 (which is mentioned again below) was used.

$$(2/3)\alpha R^2 + pR = 2\gamma_L \quad \text{Equation 3}$$

In this example, the design was carried out under a condition of using pure water.

Density and specific gravity of pure water: 1.00 (literature value)

Surface tension of a liquid $\gamma_L$: $7 \times 10^{-2}$ [g/cm]

The surface tension $\gamma_L$ of the liquid of the culture medium A can be measured by various methods such as the Wilhelmy method. Alternatively, the information can be obtained from a distributor. The contact angle θc of the pure water with respect to the material of the device measured using the droplet method was 91 degrees (cos 91 degrees=−0.017). Note that the culture medium and the pure water used in this example exhibit a value of the contact angle θc that is close to the above value.

The height H of the culture medium was designed in such a way that it is within 1 cm.

When the culture medium A is used, the above values are substituted into the equation 3 in order to calculate the equivalent radius Rout of the circumscribed circles.

$$(2/3) \times 1.00 \times R^2 + 1 \times 1.00 \times R = 2 \times 7 \times 10^{-2}$$

$$R = 0.123, -1.629$$

As the equivalent radius Rout of the circumscribed circles is a positive value, the following value was defined.

$$R = 0.123 \text{ cm} = 1230 \text{ μm}$$

The equivalent diameter Dout of the circumscribed circles was 285 μm that is 23% of the calculated value. At this time, reduced hydrophobic properties caused by absorption of protein, a force from a gravity of spheroids, and possibility that the droplets cannot be held due to culture medium exchange or a media exchange were considered. The angle θi was 67.5 degrees. Further, the openings were designed in such a way that the size of which will become 1 mm. As shown in FIG. 14, it has been designed in such a way that the device can surely hold the droplets by causing the droplets to be stopped halfway of lateral surfaces of the device. It was designed such that the diameter of 91x in FIG. 30 will become 31 mm.

Comparative Example 1

A low adhesion container, which was obtained by pasting a silicone resin (KE-1603(A/B) manufactured by Shin-Etsu Chemical Co., Ltd. on a bottom of a glass Petri-dish with a diameter of 5 cm was used.

2. Culture Method (1) A cell suspension that has been adjusted to contain 2.5 million mouse ES cells in a culture medium of 10 mL was added in a well shown in FIG. 30. These cells were cultured for two days. This cell suspension was used in both of the example and the comparative example. Note that when this cell suspension was used, the number of cells that can be poured into one opening is 1250 per opening. In other examples, the cell suspensions that have been adjusted in such a way that the number of cells poured into one opening will become 1500, 1000, and 500, respectively, were used. In these examples, the cells were cultured for two days in a manner similar to the above example.

(2) In the example, the second surface 12 was brought into contact with the culture medium, and spheroids were recovered and then observed. In the comparative example, the cell suspension was not transferred to another container, and spheroids were observed in the cultured container.

(3) Spheroids were observed by an inverted microscope, and diameters thereof were measured using an obtained image.

3. Result

Figure 31:
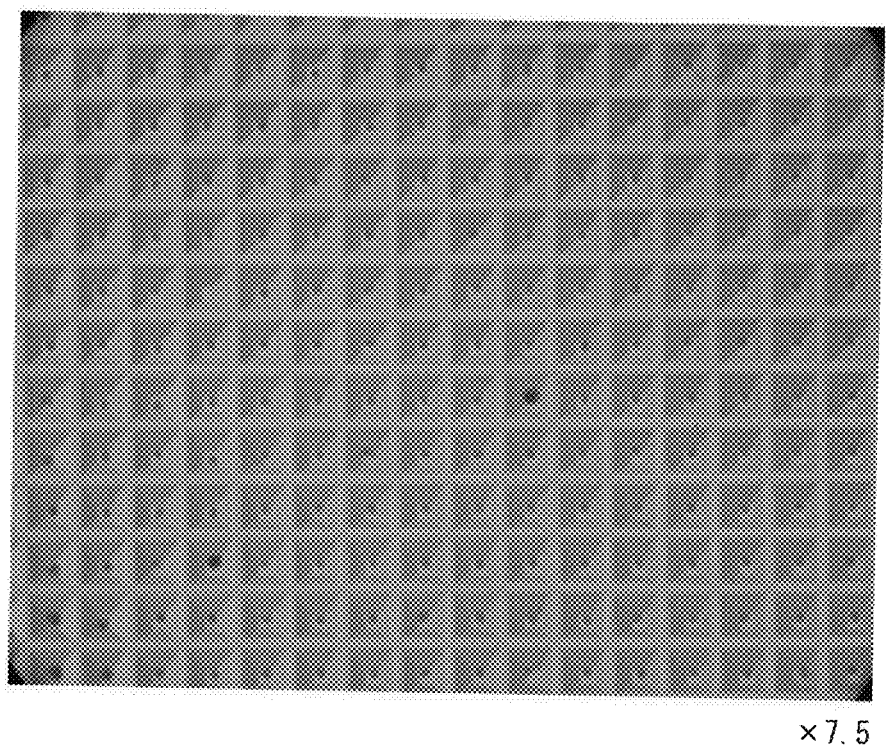
FIG. 31 is a photograph of a culture surface before spheroids are recovered in an example 1.
Figure 32:
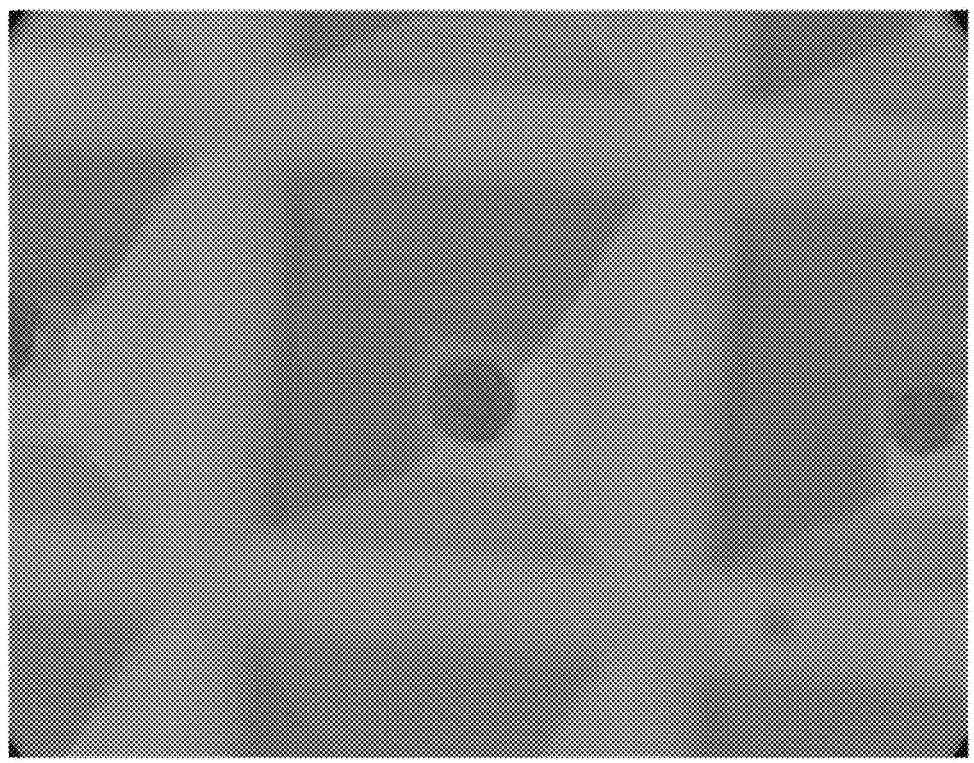
FIG. 32 is an enlarged photograph of FIG. 31.

FIGS. 31 and 32 are photomicrographs of the device and cells before the spheroids are recovered in the example 1. FIG. 32 is an enlarged photomicrograph of FIG. 31. In the example 1, spheroids were formed in the respective openings.

Figure 33:
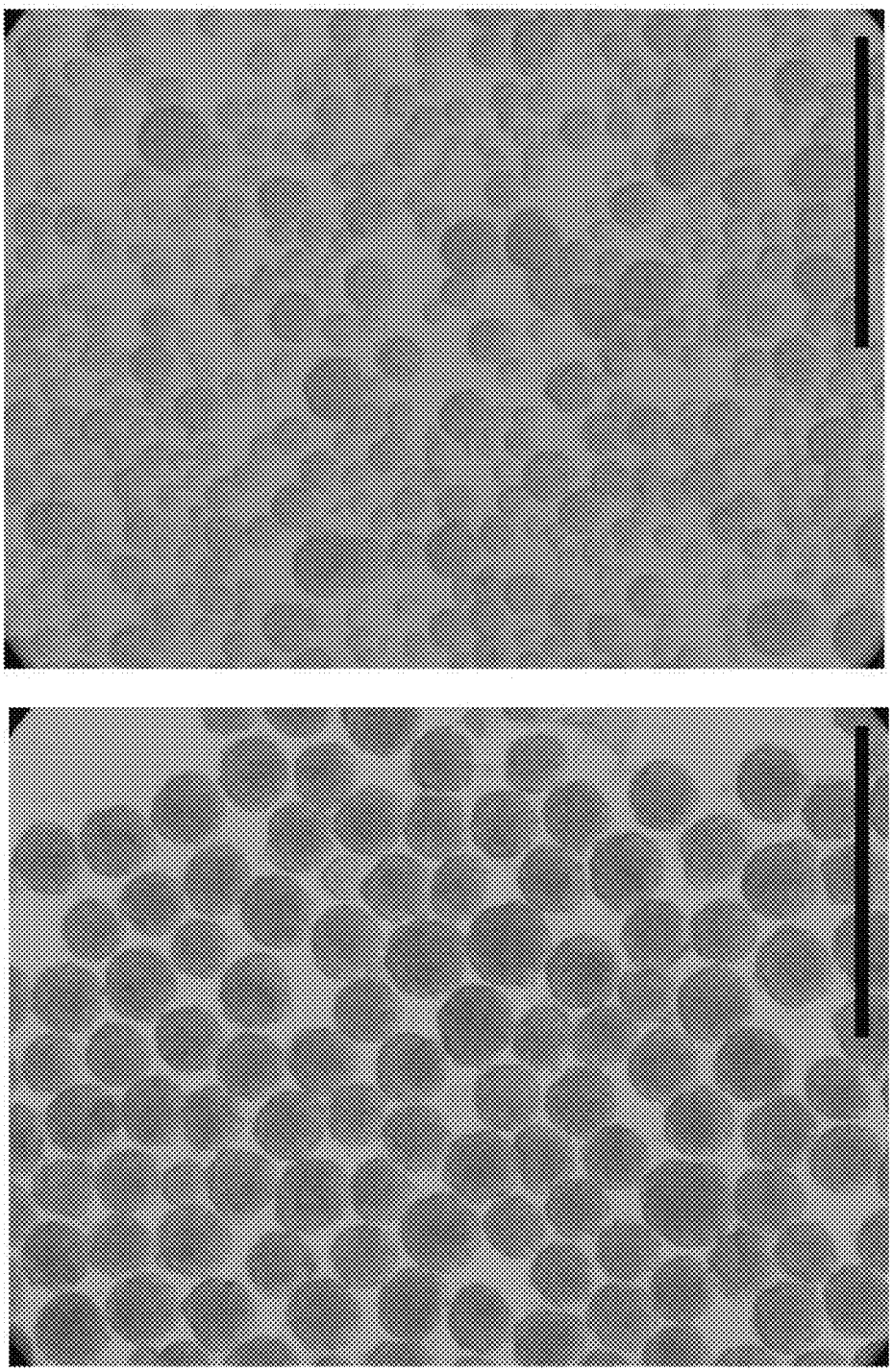
FIG. 33 is a photomicrograph of recovered spheroids according to the example 1 and the comparative example 1.

FIG. 33 is a photomicrograph of the recovered spheroids according to the example 1 and the comparative example 1.

Figure 34:
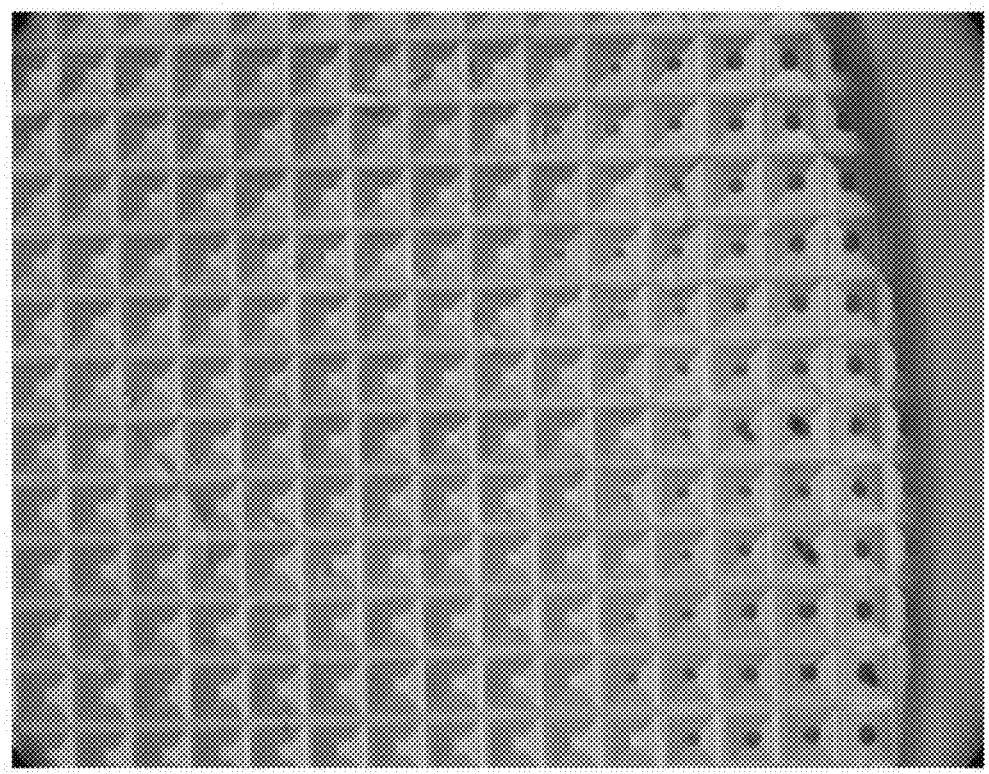
FIG. 34 is a photograph of a device surface after the spheroids are recovered in the example 1.

FIG. 34 is a photograph of a surface of the device after the spheroids were recovered in the example 1. Almost all of the remaining spheroids shown in FIG. 31 were recovered. However, there were still some spheroids remaining at the edge. The recovery rate was 95% or greater. The recovery rate was calculated by the equation (the number of openings not including cells/the total number of openings)×100.

Figure 35:
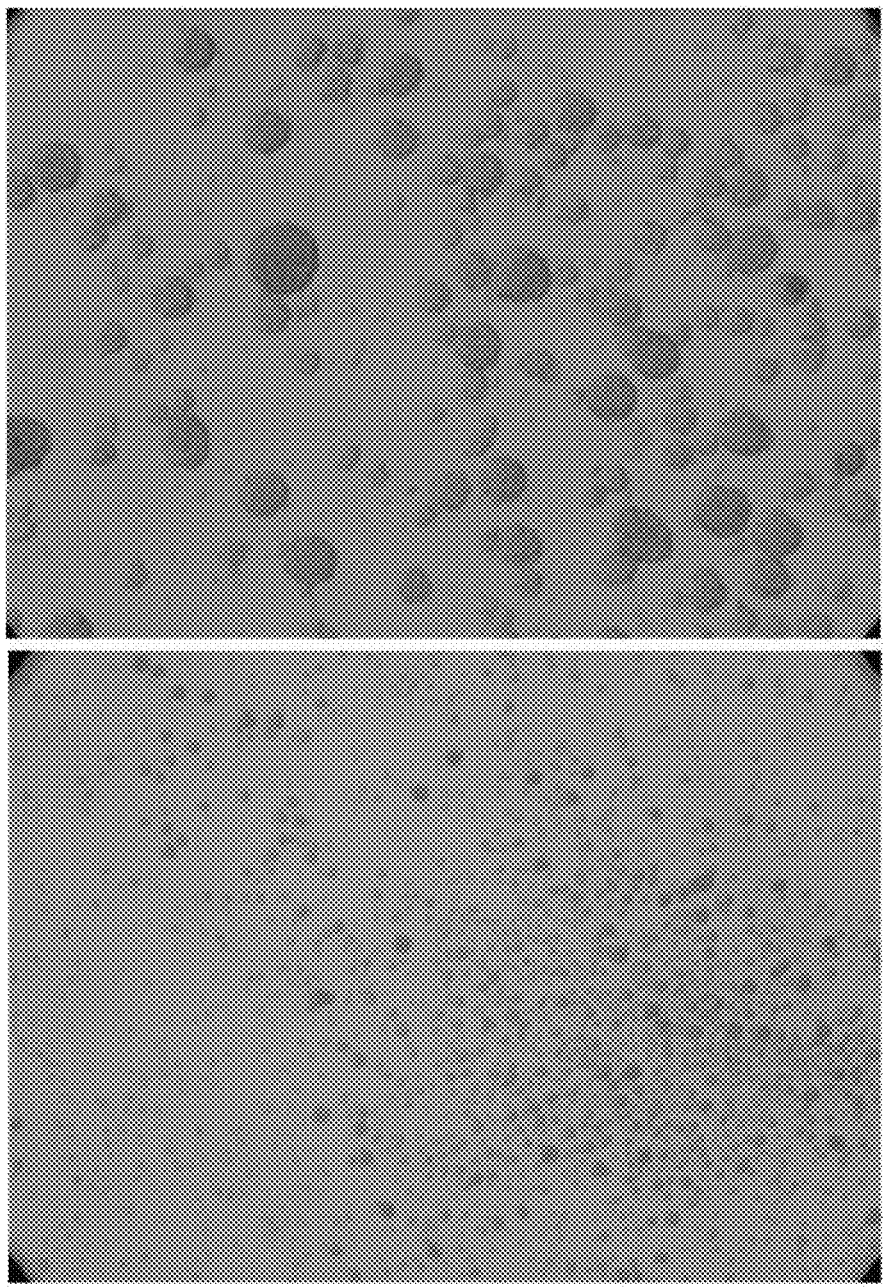
FIG. 35 is a photograph of spheroids according to the comparative example 1.

FIG. 35 is a photograph of the spheroids in the comparative example 1.

Figure 36:
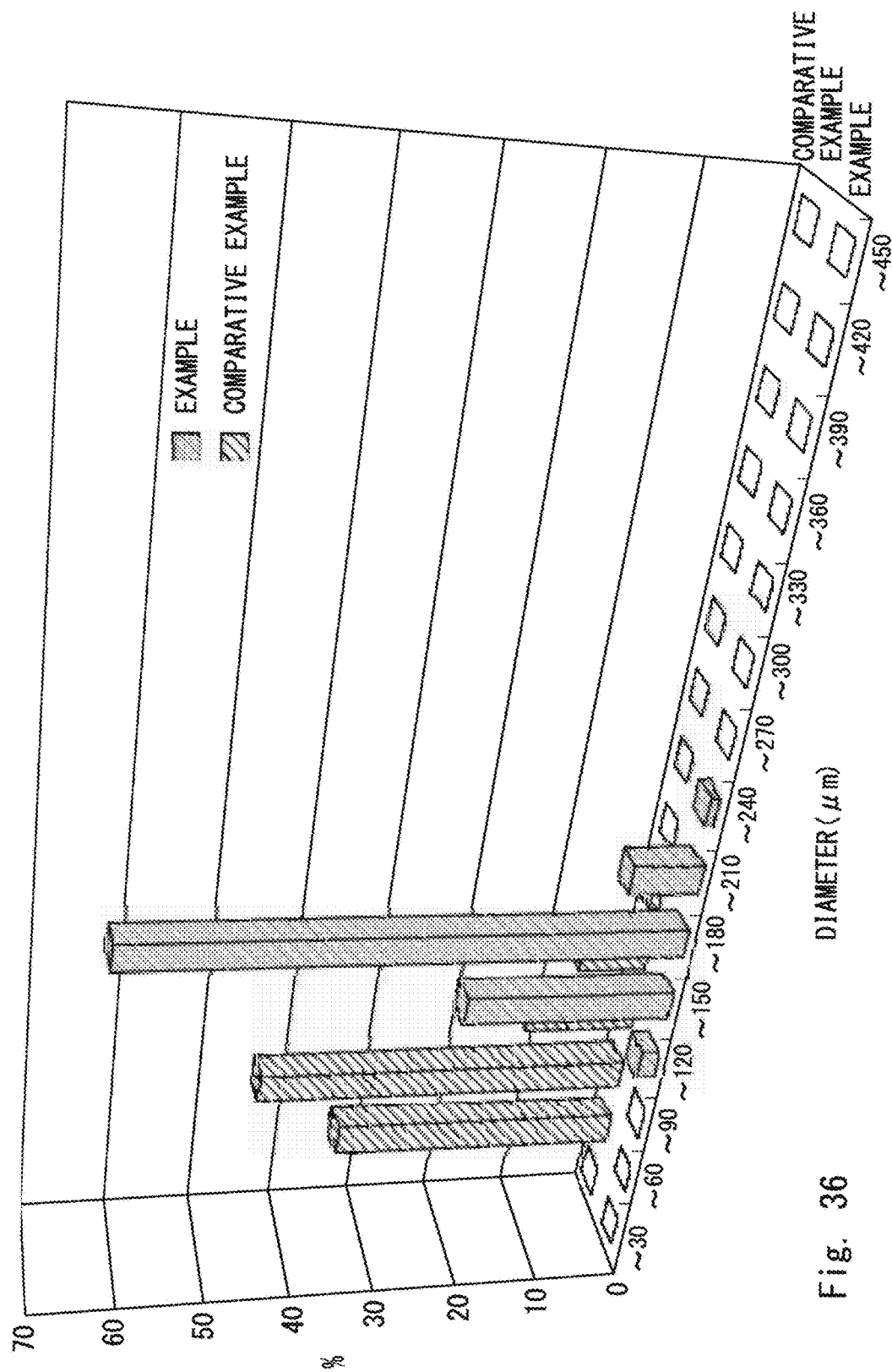
FIG. 36 is a graph showing a particle size distribution according to the example 1 and the comparative example 1.

FIG. 36 is a graph showing a particle size distribution according to the example 1 and the comparative example 1. To create the graph of FIG. 36, the spheroids were photographed using the ×75 lens of FIG. 33 (photograph in the example 1 on the left and the photograph in the comparative example 1 on the right), and images of the spheroids were captured. The number of pieces of data shown in the following table 1 was selected from the captured images, and diameters of the respective spheroids were measured.

An average value (μm), sample standard deviation (SD), and variations (that is defined by dividing SD by the average value of the diameters) of the diameters of cell aggregates are shown in the table 1. As can be seen from the value of SD/average diameter, variations in the example 1 were ⅓ or less of variations in the comparative example 1.

TABLE 1

|  | Average diameter (μm) | SD | Number of data | SD/Average diameter (%) |
|---|---|---|---|---|
| Example | 163.4 | 17.1 | 98 | 10.5 |
| Comparative example | 77.9 | 26 | 100 | 33.4 |

Figure 37:
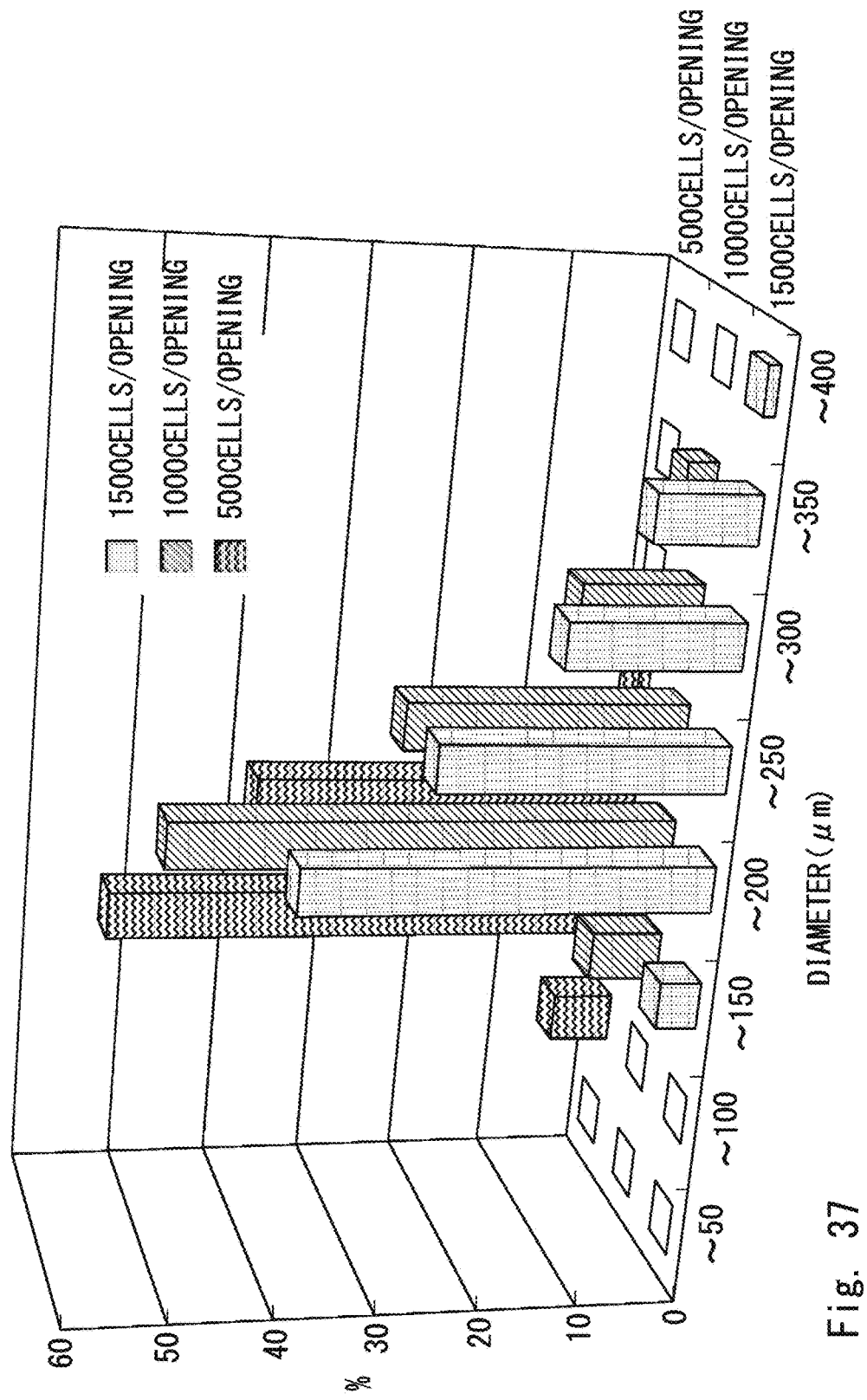
FIG. 37 is a graph showing a particle size distribution when the number of cells according to the example 1 is changed.

FIG. 37 shows a particle size distribution with different number of cells of the example 1.

An investigation was carried out as to whether or not cell aggregates with a uniform diameter can be formed even with different number of cells. Table 2 shows a result of the investigation. With the equivalent diameter D designed this time, in the cases of 1500 and 1000 cells per opening, variations were about 10% lower than those in the comparative example. In the case of 500 cells per opening, the variations were comparable to those in the comparative example.

TABLE 2

| | Average diameter (μm) | SD | Number of data | SD/Average diameter (%) |
|---|---|---|---|---|
| 1500 cells/opening | 225 | 52.5 | 554 | 23 |
| 1000 cells/opening | 201 | 47.1 | 673 | 23 |
| 500 cells/opening | 143 | 49.9 | 717 | 35 |

Note that the present invention is not limited by the above exemplary embodiments, and modifications can be made as appropriate without departing from the scope of the invention.

The present application is based upon and claims the benefit of priority from Japanese Patent Application No. 2014-034577, filed on Feb. 25, 2014, the entire contents of which are hereby incorporated by reference.

REFERENCE SIGNS LIST 1, 1a to 1h, 1x SPHEROID-PRODUCING DEVICE
7 SPHEROID
8 CULTURE MEDIUM
9 CELL. CULTURE CONTAINER
11, 11x FIRST SURFACE
12, 12x SECOND SURFACE
13, 13x WALL SURFACE
9 CELL CULTURE CONTAINER
91, 91x WELL CONTAINER
92 PETRI-DISH
93 LID

The invention claimed is:

1. A spheroid-producing hanging drop device comprising:
a top surface that forms an upper surface of the spheroid-producing device:
a bottom surface that is a back side surface of the first surface, and
that forms a bottom surface of the spheroid-producing device;
a plurality of wall surfaces extending from the top surface to the bottom surface that define a plurality of wells, each of the plurality of wells having a hole penetrating through the top surface through which cells and media are introduced into each of the plurality of wells, and a hole penetrating through the bottom surface;
wherein a width of the top surface between adjacent wall surfaces defining one of the wells is 2 mm or less;
wherein the top surface between adjacent wells are round or are conical or are polygonal cones having vertexes; and
wherein the plurality of wall surfaces are hydrophobic such that a contact angle θc between the plurality of wall surfaces and a culture medium disposed in the plurality of wells is within a range of $-1 < \cos \theta c < 0$, as measured by the droplet method.

2. The spheroid-producing hanging drop device according to claim 1, wherein the holes in the bottom surfaces of the wells are circular, and the diameter of the circular holes in the bottom surfaces of the wells is within a range of 200 micrometers to 1 cm.

3. The spheroid-producing hanging drop device according to claim 1, wherein at least portions of the wall surfaces are inclined between the top surface and the bottom surface, and make an angle greater than 30 degrees and smaller than 90 degrees with respect to the bottom surface.

4. The spheroid-producing hanging drop device according to claim 2, wherein a radius (cm) of the circular holes in the bottom surfaces of the wells is less than or equal to a value of a variable X that is defined by an equation of $$(2/3)\alpha X^2 + pX = 2\gamma_L,$$

where p is a water pressure [g/cm²] at the openings in the second surface, α is a specific gravity of the culture medium, and $\gamma_L$ [g/cm] is surface tension of the culture medium as measured by the Wilhelmy method.

5. The spheroid-producing hanging drop device according to claim 2, wherein a diameter of the circular holes in the bottom surfaces of the wells is such that the following equations are satisfied:

$$\gamma_L \cos \theta c - \gamma_S > 0$$

and $p = \gamma_L \times (2/r)$ where p is a water pressure [g/cm²] at the openings in the second surface, $\gamma_L$ is surface tension of the liquid medium [g/cm] as measured by the Wilhelmy method, r is a radius of curvature [cm], and $\gamma_S$ is surface tension of the plurality of wall surfaces [g/cm].

6. The spheroid-producing hanging drop device according to claim 1, wherein the spheroid-producing device is made of a material selected from the group consisting of acrylic resin, polylactic acid, polyglycolic acid, styrene resin, acrylic styrene copolymer resin, polycarbonate resin, polyester resin, polyvinyl alcohol resin, ethylene-vinyl alcohol copolymer resin, thermoplastic elastomer vinyl chloride resin, silicone resin, silicon resin, and combinations thereof.

7. The spheroid-producing hanging drop device according to claim 6, wherein the plurality of wall surfaces comprise functional groups formed by a surface modification treatment selected from the group consisting of plasma treatment, corona discharge, UV ozone treatment, and combinations thereof.

8. The spheroid-producing hanging drop device according to claim 6, wherein the plurality of wall surfaces are coated with a substance selected from the group consisting of inorganic substances, metal, synthetic polymers, dimers, trimers, tetramers, biobased polymers, and combinations thereof.

9. The spheroid-producing hanging drop device according to claim 7, wherein a portion of the wall surfaces comprise nanometer order microstructures.

10. The spheroid-producing device according to claim 1, wherein front surfaces of the plurality of wall surfaces comprise nanometer order microstructures.

11. The spheroid-producing hanging drop device according to claim 1, wherein the outer wall surrounding the first surface is a part of a well container.

12. The spheroid-producing device according to claim 1, wherein the spheroid-producing device is a molding made of one of or a combination of inorganic substances.

13. The spheroid-producing device according to claim 12, wherein surfaces of the plurality of wall surfaces are modified by a surface modification treatment selected from the group consisting of plasma treatment, corona discharge, UV ozone treatment, and combinations thereof.

14. The spheroid-producing device according to claim 12, wherein the plurality of wall surfaces are coated with a substance selected from the group consisting of inorganic substances, metal, polymer, dimers, trimers, tetramers, and combinations thereof.

15. A method for recovering spheroids from the spheroid-producing device according to claim 1, comprising bringing the second surface of the spheroid-producing device into contact with a solution selected from water, a culture medium, and a buffer solution in order to recover the spheroids.

16. A method for recovering spheroids from the spheroid-producing device according to claim 1, comprising applying a pressure on the first surface of the spheroid-producing device, whereby the spheroids fly out of the openings in the second surface.

17. A method for producing spheroids using the spheroid producing device according to claim 1, the method comprising:
   pouring a culture medium containing cells into the plurality of holes from the first surface;
   forming droplets in the plurality of holes; and
   culturing the cells in the droplets in order to produce the spheroids.

18. The method according to claim 17, further comprising bringing the second surface into contact with a solution selected from one of water, a culture medium, and a buffer solution in order to recover the spheroids.

19. The method according to claim 17 further comprising applying a pressure on the first surface to thereby destroy the droplets and to cause the spheroids to fly out of the openings in the second surface.

* * * * *

UNITED STATES PATENT AND TRADEMARK OFFICE
CERTIFICATE OF CORRECTION

PATENT NO. : 10,683,477 B2
APPLICATION NO. : 15/121322
DATED : June 16, 2020
INVENTOR(S) : Shoichiro Sumi Page 1 of 1

It is certified that error appears in the above-identified patent and that said Letters Patent is hereby corrected as shown below:

On the Title Page

On page 2, in Column 1, item (56), Other Publications, Line 2, delete "eguipment" and insert -- equipment --, therefor.

On page 2, in Column 1, item (56), Other Publications, Line 5, delete "eguipment" and insert -- equipment --, therefor.

In the Claims

In Column 21, Line 54, Claim 1, delete "-1<cos θc<0," and insert -- $-1 < \cos\theta c \leq 0$, --, therefor.

In Column 22, Line 3, Claim 4, delete "(2/3)αX2+pX=2γ$_L$," and insert -- $(2/3)\alpha X^2 + pX = 2\gamma_L$, --, therefor.

Signed and Sealed this
Eighth Day of September, 2020

Andrei Iancu
*Director of the United States Patent and Trademark Office*